United States Patent
Bracht

(10) Patent No.: US 11,414,469 B2
(45) Date of Patent: Aug. 16, 2022

(54) METHOD FOR PROMOTING ADIPOCYTE DIFFERENTIATION AND OBESITY-RELATED DISEASE TREATMENT

(71) Applicant: AMERICAN UNIVERSITY, Washington, DC (US)

(72) Inventor: John R. Bracht, Washington, DC (US)

(73) Assignee: American University, Washington, DC (US)

( * ) Notice: Subject to any disclaimer, the term of this patent is extended or adjusted under 35 U.S.C. 154(b) by 87 days.

(21) Appl. No.: 16/662,457

(22) Filed: Oct. 24, 2019

(65) Prior Publication Data
US 2020/0131238 A1 Apr. 30, 2020

Related U.S. Application Data

(60) Provisional application No. 62/750,488, filed on Oct. 25, 2018.

(51) Int. Cl.
| | |
|---|---|
| A61K 38/17 | (2006.01) |
| A61K 38/18 | (2006.01) |
| C07K 14/475 | (2006.01) |
| C07K 14/47 | (2006.01) |
| C12N 5/077 | (2010.01) |
| A61K 38/00 | (2006.01) |

(52) U.S. Cl.
CPC .......... C07K 14/473 (2013.01); C12N 5/0653 (2013.01); *A61K 38/00* (2013.01); *C12N 2501/13* (2013.01); *C12N 2506/1384* (2013.01)

(58) Field of Classification Search
None
See application file for complete search history.

(56) References Cited

U.S. PATENT DOCUMENTS

| | | |
|---|---|---|
| 2003/0092601 A1 | 5/2003 | Polansky |
| 2003/0129688 A1 | 7/2003 | Ballinger |
| 2012/0121557 A1 | 5/2012 | Kuhn |
| 2016/0279201 A1 | 9/2016 | Lin |
| 2019/0024054 A1 | 1/2019 | Yamamoto |

FOREIGN PATENT DOCUMENTS

| | | |
|---|---|---|
| WO | WO 2015121859 | 8/2015 |
| WO | WO 2017009263 | 1/2017 |
| WO | WO 2017069222 | 4/2017 |

OTHER PUBLICATIONS

PCT, International Searching Authority Invitation to Pay Fees, Partial PCT Search Report, International Application No. PCT/US2019/57571; dated Jan. 23, 2020, 10 pages.
Aghajanian, H. et al. Coronary vasculature patterning requires a novel endothelial ErbB2 holoreceptor. Nat Commun 7, 12038, (2016).
Ahima, R. S. Adipose tissue as an endocrine organ. Obesity 14, 242-249 (2006).
Arai, F. et al. Tie2/angiopoietin-1 signaling regulates hematopoietic stem cell quiescence in the bone marrow niche. Cell 118, 149-161, (2004).
Arner, E. et al. Adipocyte turnover: relevance to human adipose tissue morphology. Diabetes 59, 105-109, (2010).
Arner, P., Arner, E., Hammarstedt, A. & Smith, U. Genetic Predisposition for Type 2 Diabetes, but Not for Overweight/Obesity, Is Associated with a Restricted Adipogenesis. PloS one 6, e18284, (2011).
Astrup, A. & Finer, N. Redefining type 2 diabetes: 'diabesity' or 'obesity dependent diabetes mellitus'? Obesity reviews : an official journal of the International Association for the Study of Obesity 1, 57-59 (2000).
Atzmon, G. et al. Differential gene expression between visceral and subcutaneous fat depots. Horm Metab Res 34, 622-628, (2002).
Aust, L. et al. Yield of human adipose-derived adult stem cells from liposuction aspirates. Cytotherapy 6, 7-14 (2004).
Bersell, K., Arab, S., Haring, B. & Kuhn, B. Neuregulin1/ErbB4 Signaling Induces Cardiomyocyte Proliferation and Repair of Heart Injury. Cell 138, 257-270, (2009).
Biederman, M. K. et al. Discovery of the First Germline-Restricted Gene by Subtractive Transcriptomic Analysis in the Zebra Finch, Taeniopygia guttata. Current Biology 28, 1620-1627.e1625, (2018).
Blanpain, C., Lowry, W. E., Geoghegan, A., Polak, L. & Fuchs, E. Self-renewal, multipotency, and the existence of two cell populations within an epithelial stem cell niche. Cell 118, 635-648, (2004).
Bluher, M. The distinction of metabolically 'healthy' from 'unhealthy' obese individuals. Curr Opin Lipidol 21, 38-43, (2010).

(Continued)

*Primary Examiner* — Christine J Saoud
*Assistant Examiner* — Jon M Lockard
(74) *Attorney, Agent, or Firm* — Thompson Hine LLP

(57) ABSTRACT

Here we show that epigenetic control of Neuregulin-1 (NRG1) affects adipose differentiation of stem cells in vitro. Building on this finding, we established a model in which NRG1 is a white adipose tissue (WAT) specific regulator analogous to the role of NRG4 in black adipose tissue (BAT). In this light, NRG1 functions in a paracrine or autocrine manner to regulate formation of new adipocytes from stem populations, both in vitro and in vivo. In neurons, NRG1 has been shown already to play a similar role, promoting neuronal cell differentiation from progenitors in the vertebrate cortex and retina and even promoting neuronal differentiation in vitro. Similarly, in the heart, NRG1 promotes differentiation of cardiomyocytes from their stem cell progenitors both in vivo and in vitro and for this reason has been successfully tested in clinical trials for heart failure. Our model extends these findings to adipose biology and indicates that epigenetic control of NRG1 may constitute an intrinsic mechanism limiting the expansion of WAT depots, potentially elucidating important health implications for the comorbidities of obesity and providing treatment for obesity-related diseases.

18 Claims, 9 Drawing Sheets
Specification includes a Sequence Listing.

(56) References Cited

OTHER PUBLICATIONS

Boquest, A. C., Noer, A. & Collas, P. Epigenetic programming of mesenchymal stem cells from human adipose tissue. Stem Cell Rev 2, 319-329, (2006).
Caillaud, K. et al. Neuregulin 1 improves glucose tolerance in adult and old rats. Diabetes Metab 42, 96-104, (2016).
Carobbio, S., Guenantin, A. C., Samuelson, I., Bahri, M. & Vidal-Puig, A. Brown and beige fat: From molecules to physiology and pathophysiology. Biochimica et biophysica acta, (2018).
Chen, Y., Pan, R. & Pfeifer, A. Fat tissues, the brite and the dark sides. Pflugers Arch 468, 1803-1807, (2016).
Chondronikola, M. & Sidossis, L. S. Brown and beige fat: From molecules to physiology. Biochimica et biophysica acta, (2018).
Christian, M. Transcriptional fingerprinting of "browning" white fat identifies NRG4 as a novel adipokine. Adipocyte 4, 50-54, (2015).
Chusyd, D. E., Wang, D. H., Huffman, D. M. & Nagy, T. R. Relationships between Rodent white Adipose Fat Pads and Human white Adipose Fat Depots. Front Nutr 3, (2016).
Clayton, J. A. & Collins, F. S. Policy: NIH to balance sex in cell and animal studies. Nature 509, 282-283 (2014).
Cong, L. et al. Multiplex Genome Engineering Using CRISPR/Cas Systems. Science 339, 819-823, (2013).
Cotsarelis, G., Sun, T. T. & Lavker, R. M. Label-Retaining Cells Reside in the Bulge Area of Pilosebaceous Unit—Implications for Follicular Stem-Cells, Hair Cycle, and Skin Carcinogenesis. Cell 61, 1329-1337, (1990).
Dekker, J. & Mirny, L. The 3D Genome as Moderator of Chromosomal Communication, Cell 164, 1110-1121, (2016).
Denker, A. & de Laat, W. The second decade of 3C technologies: detailed insights into nuclear organization. Genes & development 30, 1357-1382, (2016).
Despres, J. P. & Lemieux, I. Abdominal obesity and metabolic syndrome. Nature 444, 881-887, (2006).
Dixon, J. R. et al. Topological domains in mammalian genomes identified by analysis of chromatin interactions. Nature 485, 376-380, (2012).
Drel, V. R. et al. The leptin-deficient (ob/ob) mouse: a new animal model of peripheral neuropathy of type 2 diabetes and obesity. Diabetes 55, 3335-3343, (2006).
Drenick, E. J., Bale, G. S., Seltzer, F. & Johnson, D. G. Excessive mortality and causes of death in morbidly obese men. Jama 243, 443-445 (1980).
Engeland, A., Bjorge, T., Sogaard, A. J. & Tverdal, A. Body mass index in adolescence in relation to total mortality: 32-year follow-up of 227,000 Norwegian boys and girls. American journal of epidemiology 157, 517-523 (2003).
Ennequin, G. et al. Neuregulin 1 affects leptin levels, food intake and weight gain in normal-weight, but not obese, db/db mice. Diabetes Metab 41, 168-172, (2015).
Ennequin, G. et al. Neuregulin 1 improves complex 2-mediated mitochondrial respiration in skeletal muscle of healthy and diabetic mice. Sci Rep 7, 1742, (2017).
Ennequin, G. et al. Neuregulin 1 Improves Glucose Tolerance in db/db Mice. PloS one 10, e0130568, (2015).
Falls, D. L. Neuregulins: functions, forms, and signaling strategies. Exp Cell Res 284, 14-30, (2003).
Ferrario, C. et al. Metallothionein 1G acts as an oncosupressor in papillary thyroid carcinoma. Lab Invest 88, 474-481, (2008).
Friend, D. M. et al. Basal Ganglia Dysfunction Contributes to Physical Inactivity in Obesity. Cell Metab 25, 312-321, (2017).
Frohling, S. et al. Identification of driver and passenger mutations of FLT3 by high-throughput DNA sequence analysis and functional assessment of candidate alleles. Cancer Cell 12, 501-513, (2007).
Frontini, A. & Cinti, S. Distribution and Development of Brown Adipocytes in the Murine and Human Adipose Organ, Cell Metabolism 11, 253-256, (2010).
Gao, R. et al. A Phase II, randomized, double-blind, multicenter, based on standard therapy, placebo-controlled study of the efficacy and safety of recombinant human neuregulin-1 in patients with chronic heart failure. J Am Coll Cardiol 55, 1907-1914, (2010).
Geisberg, C. A. et al. Circulating neuregulin-1beta levels vary according to the angiographic severity of coronary artery disease and ischemia. Coron Artery Dis 22, 577-582, (2011).
Goncalves, C. G., Glade, M. J. & Meguid, M. M. Metabolically healthy obese individuals: Key protective factors. Nutrition 32, 14-20, (2016).
Gondor, A., Rougier, C. & Ohlsson, R. High-resolution circular chromosome conformation capture assay. Nat Protoc 3, 303-313, (2008).
Green, H. & Meuth, M. An established pre-adipose cell line and its differentiation in culture. Cell 3, 127-133 (1974).
Gustafson, B. & Smith, U. Regulation of white adipogenesis and its relation to ectopic fat accumulation and cardiovascular risk. Atherosclerosis 241, 27-35, (2015).
Gustafson, B. & Smith, U. The WNT inhibitor Dickkopf 1 and bone morphogenetic protein 4 rescue adipogenesis in hypertrophic obesity in humans. Diabetes 61, 1217-1224, (2012).
Gustafson, B., Hedjazifar, S., Gogg, S., Hammarstedt, A. & Smith, U. Insulin resistance and impaired adipogenesis. Trends Endocrin Met 26, 193-200, (2015).
Herrero, A., Casar, B., Colon-Bolea, P., Agudo-Ibanez, L. & Crespo, P. Defined spatiotemporal features of RASERK signals dictate cell fate in MCF-7 mammary epithelial cells. Molecular biology of the cell 27, 1958-1968, (2016).
Hilton, I. B. et al. Epigenome editing by a CRISPR-Cas9-based acetyltransferase activates genes from promoters and enhancers. Nature biotechnology 33, 510-517 (2015).
Ingalls, A. M., Dickie, M. M. & Snell, G. D. Obese, a new mutation in the house mouse. J Hered 41, 317-318 (1950).
Isakson, P., Hammarstedt, A., Gustafson, B. & Smith, U. Impaired preadipocyte differentiation in human abdominal obesity: role of Wnt, tumor necrosis factor-alpha, and inflammation. Diabetes 58, 1550-1557, (2009).
Iwakura, Y. & Nawa, H. ErbB1-4-dependent EGF/neuregulin signals and their cross talk in the central nervous system: pathological implications in schizophrenia and Parkinson's disease. Front Cell Neurosci 7, 4, (2013).
Jabbour, A. et al. Parenteral administration of recombinant human neuregulin-1 to patients with stable chronic heart failure produces favourable acute and chronic haemodynamic responses. Eur J Heart Fail 13, 83-92, (2011).
Jian, X. & Felsenfeld, G. Insulin promoter in human pancreatic beta cells contacts diabetes susceptibility loci and regulates genes affecting insulin metabolism. Proceedings of the National Academy of Sciences of the United States of America 115, E4633-E4641, (2018).
Jinek, M. et al. RNA-programmed genome editing in human cells. Elife 2, (2013).
Jones, P. A. & Taylor, S. M. Cellular differentiation, cytidine analogs and DNA methylation. Cell 20, 85-93 (1980).
Jun, H. et al. An immune-beige adipocyte communication via nicotinic acetylcholine receptor signaling. Nat Med 24, 814-822, (2018).
Kalari, S. & Pfeifer, G. P. Identification of Driver and Passenger DNA Methylation in Cancer by Epigenomic Analysis. Adv Genet 70, 277-308, (2010).
Karastergiou, K. & Fried, S. K. Cellular Mechanisms Driving Sex Differences in Adipose Tissue Biology and Body Shape in Humans and Mouse Models. Adv Exp Med Biol 1043, 29-51, (2017).
Kern, M. et al. C57BL/6JRj mice are protected against diet induced obesity (DIO). Biochemical and biophysical research communications 417, 717-720, (2012).
Kim, J. Y. et al. Obesity-associated improvements in metabolic profile through expansion of adipose tissue. Journal of Clinical Investigation 117, 2621-2637, (2007).
Kloting, N. et al. Insulin-sensitive obesity. Am J Physiol Endocrinol Metab 299, E506-515, (2010).
Kolovos, P. et al. Targeted Chromatin Capture (T2C): a novel high resolution high throughput method to detect genomic interactions and regulatory elements. Epigenet Chromatin 7, (2014).
Kovacs, T., Bansagi, B., Kelemen, O. & Keri, S. Neuregulin 1-Induced AKT and ERK Phosphorylation in Patients with Fragile

(56) References Cited

OTHER PUBLICATIONS

X Syndrome (FXS) and Intellectual Disability Associated with Obstetric Complications. J Mol Neurosci 54, 119-124, (2014).
Kwan, R., Looi, K. & Omary, M. B. Absence of keratins 8 and 18 in rodent epithelial cell lines associates with keratin gene mutation and DNA methylation: Cell line selective effects on cell invasion. Exp Cell Res 335, 12-22, (2015).
Kwon, D. Y., Zhao, Y. T., Lamonica, J. M. & Zhou, Z. Locus-specific histone deacetylation using a synthetic CRISPR-Cas9-based HDAC. Nat Commun 8, (2017).
Law, J. A. & Jacobsen, S. E. Establishing, maintaining and modifying DNA methylation patterns in plants and animals. Nature reviews. Genetics 11, 204-220, (2010).
Ledford, H. CRISPR: gene editing is just the beginning. Nature 531, 156-159, (2016).
Lessard, J. et al. Low abdominal subcutaneous preadipocyte adipogenesis is associated with visceral obesity, visceral adipocyte hypertrophy, and a dysmetabolic state. Adipocyte 3, 197-205, (2014).
Li, L. & Clevers, H. Coexistence of quiescent and active adult stem cells in mammals. Science 327, 542-545, (2010).
Licholai, J. A. et al. Why Do Mice Overeat High-Fat Diets? How High-Fat Diet Alters the Regulation of Daily Caloric Intake in Mice. Obesity 26, 1026-1033, (2018).
Liu, X. S. et al. Editing DNA Methylation in the Mammalian Genome. Cell 167, 233-247 e217, (2016).
Lomvardas, S. et al. Interchromosomal interactions and olfactory receptor choice. Cell 126, 403-413, (2006).
Ma, Y., Gao, M. & Liu, D. Preventing High Fat Diet-induced Obesity and Improving Insulin Sensitivity through Neuregulin 4 Gene Transfer. Sci Rep 6, 26242, (2016).
Mali, P. et al. RNA-guided human genome engineering via Cas9. Science 339, 823-826, (2013).
Matikainen-Ankney, B. A. & Kravitz, A. V. Persistent effects of obesity: a neuroplasticity hypothesis. Ann N Y Acad Sci, (2018).
McDonald, J. I. et al. Reprogrammable CRISPR/Cas9-based system for inducing site-specific DNA methylation. Biol Open 5, 866-874, (2016).
Mei, L. & Xiong, W. C. Neuregulin 1 in neural development, synaptic plasticity and schizophrenia. Nat Rev Neurosci 9, 437-452, (2008).
Mikkelsen, T. S. et al. Comparative epigenomic analysis of murine and human adipogenesis. Cell 143, 156-169, (2010).
Mira, H. et al. Signaling through BMPR-IA Regulates Quiescence and Long-Term Activity of Neural Stem Cells in the Adult Hippocampus. Cell Stem Cell 7, 78-89, (2010).
Moondra, V. et al. Serum Neuregulin-1beta as a Biomarker of Cardiovascular Fitness. Open Biomark J 2, 1-5, (2009).
Muir, L. A. et al. Adipose tissue fibrosis, hypertrophy, and hyperplasia: Correlations with diabetes in human obesity. Obesity (Silver Spring) 24, 597-605, (2016).
Nagashima, T. et al. Quantitative transcriptional control of ErbB receptor signaling undergoes graded to biphasic response for cell differentiation. The Journal of biological chemistry 282, 4045-4056, (2007).
National Institutes of Health Guidelines on Human Subjects Research. https://humansubjects.nih.gov/walkthrough-investigator#tabpanel11. (2018).
Nguyen, K. P. et al. Feeding Experimentation Device (FED): Construction and Validation of an Open-source Device for Measuring Food Intake in Rodents. Journal of visualized experiments : JoVE, (2017).
Noer, A., Sorensen, A. L., Boquest, A. C. & Collas, P. Stable CpG hypomethylation of adipogenic promoters in freshly isolated, cultured, and differentiated mesenchymal stem cells from adipose tissue. Molecular biology of the cell 17, 3543-3556, (2006).
Ogden, C. L., Carroll, M. D., Kit, B. K. & Flegal, K. M. Prevalence of childhood and adult obesity in the United States, 2011-2012. Jama 311, 806-814, (2014).
Ortega, F. B. et al. The intriguing metabolically healthy but obese phenotype: cardiovascular prognosis and role of fitness. Eur Heart J 34, 389-397, (2013).
Paffhausen, E. S. et al. Discovery of a stem-like multipotent cell fate. American Journal of Stem Cells 7, 25-37 (2018).
Parlee, S. D., Lentz, S. I., Mori, H. & MacDougald, O. A. Quantifying size and number of adipocytes in adipose tissue. Methods Enzymol 537, 93-122, (2014).
Pascual-Serrano, A. et al. Grape seed proanthocyanidin supplementation reduces adipocyte size and increases adipocyte number in obese rats. Int J Obesity 41, 1246-1255, (2017).
Pellegrinelli, V., Carobbio, S. & Vidal-Puig, A. Adipose tissue plasticity: how fat depots respond differently to pathophysiological cues. Diabetologia 59, 1075-1088, (2016).
Pirotte, D., Wislet-Gendebien, S., Cloes, J. M. & Rogister, B. Neuregulin-1 modulates the differentiation of neural stem cells in vitro trough an interaction with the Swi/Snf complex. Mol Cell Neurosci 43, 72-80, (2010).
Poirier, P. & Eckel, R. H. Obesity and cardiovascular disease. Current atherosclerosis reports 4, 448-453 (2002).
Potten, C. S., Booth, C. & Pritchard, D. M. The intestinal epithelial stem cell: the mucosal governor, Int J Exp Pathol 78, 219-243, (1997).
Raviram, R. et al. 4C-ker: A Method to Reproducibly Identify Genome-Wide Interactions Captured by 4C-Seq Experiments. PLoS Comput Biol 12, e1004780, (2016).
Reaven, G. M. Role of insulin resistance in human disease (syndrome X): an expanded definition. Annual review of medicine 44, 121-131, (1993).
Reznikoff, C. A., Bertram, J. S., Brankow, D. W. & Heidelberger, C. Quantitative and qualitative studies of chemical transformation of cloned C3H mouse embryo cells sensitive to postconfluence inhibition of cell division. Cancer Res 33, 3239-3249 (1973).
Roberts, D. L., Dive, C. & Renehan, A. G. Biological mechanisms linking obesity and cancer risk: new perspectives. Annual review of medicine 61, 301-316, (2010).
Rothbart, S. B. & Strahl, B. D. Interpreting the language of histone and DNA modifications. Biochimica et biophysica acta 1839, 627-643, (2014).
Rupert, C. E. & Coulombe, K. L. The roles of neuregulin-1 in cardiac development, homeostasis, and disease. Biomark Insights 10, 1-9, (2015).
Sato, T. et al. Neuregulin 1 Type II-ErbB Signaling Promotes Cell Divisions Generating Neurons from Neural Progenitor Cells in the Developing Zebrafish Brain. PloS one 10, (2015).
Schmid, R. S. et al. Neuregulin 1-erbB2 signaling is required for the establishment of radial glia and their transformation into astrocytes in cerebral cortex. Proceedings of the National Academy of Sciences of the United States of America 100, 4251-4256, (2003).
Smith, J. K. Exercise, Obesity and CNS Control of Metabolic Homeostasis: A Review. Front Physiol 9, 574, (2018).
Snel, M. et al. Ectopic Fat and Insulin Resistance: Pathophysiology and Effect of Diet and Lifestyle Interventions. Int J Endocrinol, (2012).
Snodgrass-Belt, P., Gilbert, J. L. & Davis, F. C. Central administration of transforming growth factor-alpha and neuregulin-1 suppress active behaviors and cause weight loss in hamsters. Brain Res 1038, 171-182, (2005).
Sorensen, A. L., Jacobsen, B. M., Reiner, A. H., Andersen, I. S. & Collas, P. Promoter DNA Methylation Patterns of Differentiated Cells Are Largely Programmed at the Progenitor Stage. Molecular biology of the cell 21, 2066-2077, (2010).
Splinter, E., de Wit, E., van de Werken, H. J. G., Klous, P. & de Laat, W. Determining long-range chromatin interactions for selected genomic sites using 4C-seq technology: From fixation to computation. Methods 58, 221-230, (2012).
Taha, M. F. & Hedayati, V. Isolation, identification and multipotential differentiation of mouse adipose tissue derived stem cells. Tissue Cell 42, 211-216, (2010).
Tahiliani, M. et al. Conversion of 5-methylcytosine to 5-hydroxymethylcytosine in mammalian DNA by MLL partner TET1. Science 324, 930-935, (2009).

(56) References Cited

OTHER PUBLICATIONS

Takada, H. et al. Methylome, transcriptome, and PPARgamma cistrome analyses reveal two epigenetic transitions in fat cells. Epigenetics : official journal of the DNA Methylation Society 9, 1195-1206, (2014).

Tang, Q. Q. & Lane, M. D. Adipogenesis: From Stem Cell to Adipocyte. Annu Rev Biochem 81, 715-736, (2012).

Tchkonia, T. et al. Mechanisms and Metabolic Implications of Regional Differences among Fat Depots. Cell Metabolism 17, 644-656, (2013).

Tchoukalova, Y. D. et al. Subcutaneous adipocyte size and body fat distribution. The American journal of clinical nutrition 87, 56-63 (2008).

Tchoukalova, Y., Koutsari, C. & Jensen, M. Committed subcutaneous preadipocytes are reduced in human obesity. Diabetologia 50, 151-157, (2007).

Todaro, G. J. & Green, H. Quantitative studies of the growth of mouse embryo cells in culture and their development into established lines. The Journal of cell biology 17, 299-313 (1963).

Tschop, M. H. et al. A guide to analysis of mouse energy metabolism. Nat Methods 9, 57-63, (2011).

Van de Werken, H. J. et al. Robust 4C-seq data analysis to screen for regulatory DNA interactions. Nat Methods 9, 969-972, (2012).

Van den Dungen, M. W., Murk, A. J., Kok, D. E. & Steegenga, W. T. Comprehensive DNA Methylation and Gene Expression Profiling in Differentiating Human Adipocytes. Journal of Cellular Biochemistry (2016).

Van Harmelen, V. et al. Leptin secretion from subcutaneous and visceral adipose tissue in women. Diabetes 47, 913-917 (1998).

Virtue, S. & Vidal-Puig, A. Adipose tissue expandability, lipotoxicity and the Metabolic Syndrome—an allostatic perspective. Biochimica et biophysica acta 1801, 338-349, (2010).

Virtue, S. & Vidal-Puig, A. It's not how fat you are, it's what you do with it that counts. PLoS Biol 6, e237, (2008).

Vojta, A. et al. Repurposing the CRISPR-Cas9 system for targeted DNA methylation. Nucleic acids research, gkw159 (2016).

Wang, Y. H. et al. Microporation Is a Valuable Transfection Method for Gene Expression in Human Adipose Tissue-derived Stem Cells. Mol Ther 17, 302-308, (2009).

Wang, Z. et al. Neuregulin-1 enhances differentiation of cardiomyocytes from embryonic stem cells. Med Biol Eng Comput 47, 41-48, doi:10.1007/s11517-008-0383-2 (2009).

Winzell, M. S. & Ahren, B. The high-fat diet-fed mouse: a model for studying mechanisms and treatment of impaired glucose tolerance and type 2 diabetes. Diabetes 53 Suppl 3, S215-219 (2004).

Wurtele, H. & Chartrand, P. Genome-wide scanning of HoxB1-associated loci in mouse ES cells using an open-ended Chromosome Conformation Capture methodology. Chromosome Res 14, 477-495, (2006).

Xu, X. et al. A CRISPR-based approach for targeted DNA demethylation. Cell Discov 2, 16009, (2016).

Yamamoto, N. et al. Isolation of multipotent stem cells from mouse adipose tissue. J Dermatol Sci 48, 43-52, (2007).

Zhang, L. et al. DNA Methylation Landscape Reflects the Spatial Organization of Chromatin in Different Cells. Biophys J 113, 1395-1404, (2017).

Zhang, L., Komurov, K., Wright, W. E. & Shay, J. W. Identification of novel driver tumor suppressors through functional interrogation of putative passenger mutations in colorectal cancer, Int J Cancer 132, 732-737, (2013).

Zhao, Z. et al. Circular chromosome conformation capture (4C) uncovers extensive networks of epigenetically regulated intra- and interchromosomal interactions. Nature genetics 38, 1341-1347, (2006).

Zuk, P. A. et al. Human adipose tissue is a source of multipotent stem cells. Molecular biology of the cell 13, 4279-4295, (2002).

Cawthorn, William P. et al.; "Adipose tissue stem cells meet preadipocyte commitment: going back to the future"; Journal of Lipid Research; vol. 53, pp. 227-246 (2012).

Ferrero, Radiana et al.; "Toward a Consensus View of Mammalian Adipocyte Stem and Progenitor Cell Heterogeneity"; Cell Press Reviews; Trends in Cell Biology; vol. 30, No. 12; pp. 937-950 (Dec. 2020).

U.S. Patent and Trademark Office, International Search Report and Written Opinion, International Application No. PCT/US2019/057571, 10 pages, dated Jan. 23, 2020.

Zuk, P.A. et al., "Multilineage Cells from Human Adipose Tissue: Implications for Cell-Based Therapies," *Tissue Engineering*, vol. 7, No. 2, pp. 211-228, 2001.

FIG. 3 (con't)
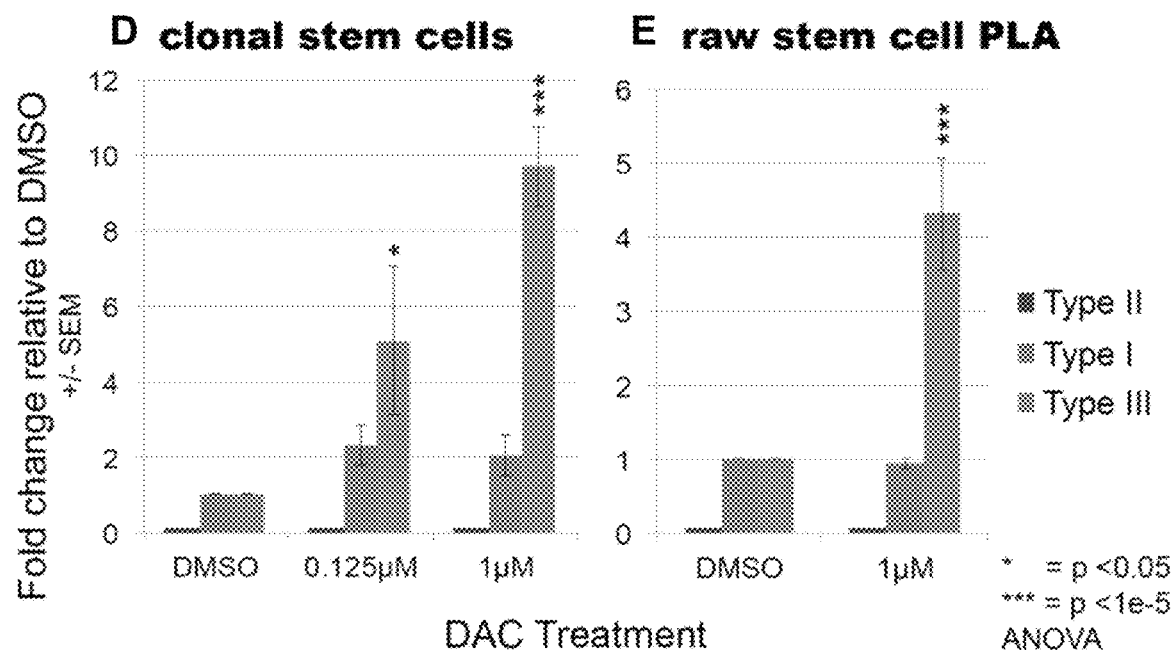

METHOD FOR PROMOTING ADIPOCYTE DIFFERENTIATION AND OBESITY-RELATED DISEASE TREATMENT

ACKNOWLEDGMENT OF GOVERNMENT SUPPORT

This invention was made with Government support under Grant No. 1K22CA184297, awarded by NIH/National Cancer Institute. The government has certain rights in the invention.

FIELD OF THE INVENTION

Provided is a method for promoting adipocyte differentiation comprising administration of Neuregulin-1. Further provided is a method of treatment for obesity-related disease comprising induction of adipocyte differentiation by Neuregulin-1.

BACKGROUND

Slightly over one-third (35%) of adults in the United States are obese, predisposing them to significant health problems including type 2 diabetes, cardiovascular disease, cancer, and increased risk of death. Obesity comes in two basic types, distinguished by adipocyte size, adipocyte number, location of fat accumulation, and risk for comorbidities. These have been classified broadly as hyperplastic (having many fat cells) and hypertrophic (fewer but larger fat cells) obesity, and although in principle both have increased body fat, the two types are not equivalent in health outcomes (See FIG. 1). Hypertrophic obesity is associated with significantly worse health outcomes and a markedly higher risk of diabetes, hypertension, and dyslipidemia (or 'Metabolic Syndrome'), while hyperplastic obesity can be comparatively benign.

Expanding fat mass requires either increased adipocyte size (hypertrophy) or increased adipocyte number (hyperplasia). Mechanisms that regulate adipocyte lipid storage permit hypertrophy with increased nutrient load. However, large, hypertrophic adipocytes face limits of expansion based on multiple factors, including hypoxia and differential matrix mechanics that result in dysfunctional adipocytes. Genetic mouse models to test these expansion limits by targeting HIF-1α targets, reducing ECM deposition, or protecting adipocytes from fatty acid oxidation have been successful in demonstrating "healthy" hypertrophy. Alternatively, adipocyte hyperplasia may present a mechanism for healthy fat storage capacity. Mature adipocytes are terminally differentiated cells. However, adipocyte precursors have been identified in adipose tissue that differentiate into fully mature white adipocytes under metabolic stimulation or PPARγ activation, both in vitro and in the mouse.

In addition to adipocyte size, the distribution of fat is different in the two obesity types: hypertrophically obese individuals tend to accumulate large amounts of fat in the visceral regions (in body cavities) and internal organs, rather than under the skin (subcutaneous fat). This can be seen in rodent models. The famous obese ob/ob mouse model (leptin mutant) displays a hypertrophic adiposity complete with fatty liver and metabolic disorders: insulin resistance, dyslipidemia, and high blood sugar. Remarkably, increasing subcutaneous adipocytes in this ob/ob background produced an even more obese mouse (morbidly obese), but reversed all metabolic problems: an engineered hyperplastic, healthy obesity. In human, visceral adiposity is correlated with lower adipose differentiation capacity from subcutaneous depots, and poorer metabolic health. The implication is that how much fat an individual is carrying is not the only relevant factor: the location and characteristics (like adipocyte size) are extremely important in health and capacity for formation of new adipocytes in subcutaneous depots is a critical determining factor of overall health.

Adipose cells play several critical roles in systemic metabolism and physiology. There are at least two classes of fat cells—white and brown. White fat is specialized to store energy in the form of triglycerides, an especially efficient method because this class of molecules is highly energetic and stored anhydrously. On fasting, the release of fatty acids and glycerol to provide fuel for the rest of the body occurs via enzymatic hydrolysis called lipolysis. These crucial functions of fat, storage, and release of fatty acids are tightly controlled by the key hormones of the fed and fasted states—insulin and catecholamines. In addition to these classic functions, the importance of white fat tissue as a central signaling node in systemic metabolism was first identified by the cloning of adipsin and leptin, two important "adipokines". In fact, fat cells and fat tissues secrete many molecules with crucial roles in metabolism, including tumor necrosis factor α (TNF-α), adiponectin, resistin, and RBP4, among others. Healthy and robust adipose development is absolutely required for proper metabolic control. Of importance, defects in adipose differentiation do not lead to healthy, lean animals but instead to lipodystrophy, a serious disease by which other tissues, especially the liver, subsume the function of fat storage, with deleterious effects, including insulin resistance, diabetes, hepatomegaly, and hypertriglyceridemia.

In contrast to white fat, brown fat is specialized to dissipate chemical energy in the form of heat, defending mammals against hypothermia. It does so by running futile metabolic cycles, most notably the futile cycle of proton exclusion from and leak back into the mitochondrial matrix via the electron transport chain and uncoupling protein 1 (UCP1). UCP1 expression is strictly limited to brown and beige fat cells. Recently, a separate futile cycle involving creatine phosphorylation/dephosphorylation was identified in mitochondria of beige fat cells, a type of brown-like adipocyte. Of importance, brown fat, in all of its dimensions, plays a role in defending animals against metabolic diseases such as obesity, type 2 diabetes, and hepatic steatosis (the earliest manifestation of nonalcoholic fatty liver disease [NAFLD]). The first evidence in this regard was the observation that mice with genetically ablated UCP1+ cells are prone to obesity and diabetes, whereas those with genetically elevated brown fat function are markedly protected from the same disorders.

Neuregulin-1 is a transmembrane protein that has multiple isoforms resulting from splice variants and is known to show agonist activity with the EGFR (or ErbB) family of tyrosine kinase receptors. It appears to be involved in a variety of functions, including cardiomyocyte protection and mental health disorders. As such, it has been tested in clinical trials for recovery from heart attacks and for depression and schizophrenia.

The adipose tissue expandability hypothesis, described herein, provides a model onto which the present invention is based. The hypothesis states that when excess energy cannot be stored in subcutaneous fat depots (i.e., more adipocytes cannot be formed), the existing adipocytes compensate by becoming larger (storing more lipid per cell), and lipids are also stored in other body regions (ectopically). It is the ability to differentiate new adipocytes from preadipocytes that determines the limits of subcutaneous adipose tissue expandability. However, the precise nature of this limiting mechanism has been unknown. Understanding this 'limiting mechanism' is a critical one since promoting subcutaneous adipose expansion may be an effective therapeutic strategy for obesity and metabolic disease.

In this application, we show that a stem cell-intrinsic epigenetic 'rheostat' tightly regulates adipose expandability, controlling the switch between hyperplastic vs. hypertrophic obesity and metabolic disease vs. health. In our model, DNA methylation directly regulates adipose expandability by limiting subcutaneous adipose differentiation. Central to the rheostat is the epigenetically regulated gene Neuregulin-1 (NRG1) (FIG. 1B).

SUMMARY

In one aspect, a method for differentiating preadipocytes into adipocytes is provided, where the method comprising exposing the preadipocytes to Neuregulin-1 followed by conditions sufficient to promote differentiation of the preadipocytes into adipocytes. In one embodiment, the Neuregulin-1 is NRG1 β. In one embodiment, the NRG1 β is the Type III isoform of NRG1 β. In one embodiment, the Neuregulin-1 is a fragment of NRG1 β comprising an EGF-binding domain. In one embodiment, the fragment of NRG1 β is SEQ ID NO: 1. In one embodiment, the Neuregulin-1 is provided at a concentration of about 1 ng/ml to about 500 ng/ml. In one embodiment, the adipocyte is a white adipose tissue (WAT) adipocyte. In one embodiment, the method is performed in vitro and in one embodiment thereof, the preadipocytes are Adipose-derived Stem Cells (ASCs), obtained from lipoaspirates. In another embodiment, the method is performed in vivo and in an embodiment thereof, the differentiation of the preadipocytes into adipocytes results in an increase in the number of adipocytes. As a result, in one embodiment, the increase in the number of adipocytes results in at least one of decreased blood sugar, increased insulin sensitivity, decreased hypertension, resolution of hyperlipidemia, and lowered bodyweight.

DETAILED DESCRIPTION

Figure 1A:
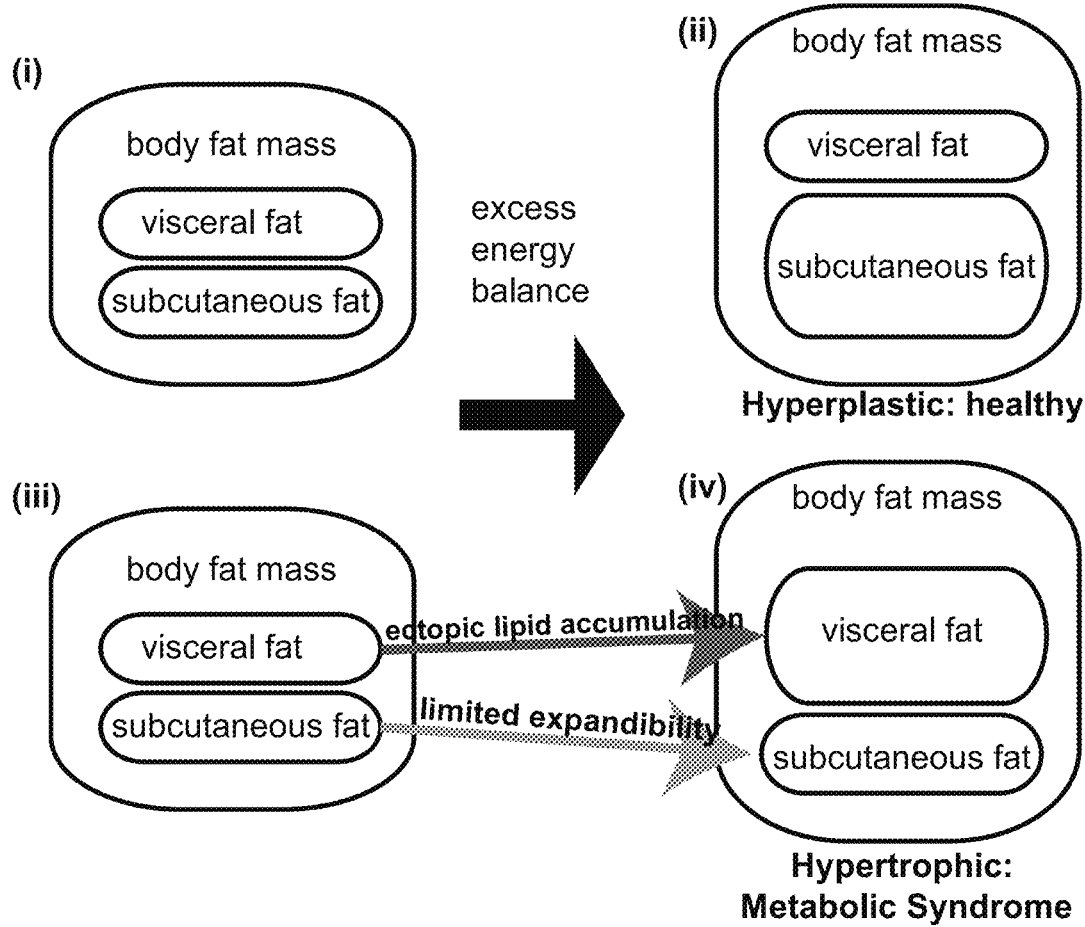
FIG. 1A shows adipose tissue expandability hypothesis. (i-ii), Hyperplastic obesity: under conditions of excess energy balance, subcutaneous adipose tissue expands. Associated with relative health. (iii-iv), Hypertrophic obesity: subcutaneous adipose tissue depots reaches an expandability limit, leading to ectopic adipose deposits, causing metabolic syndrome.
Figure 1B:
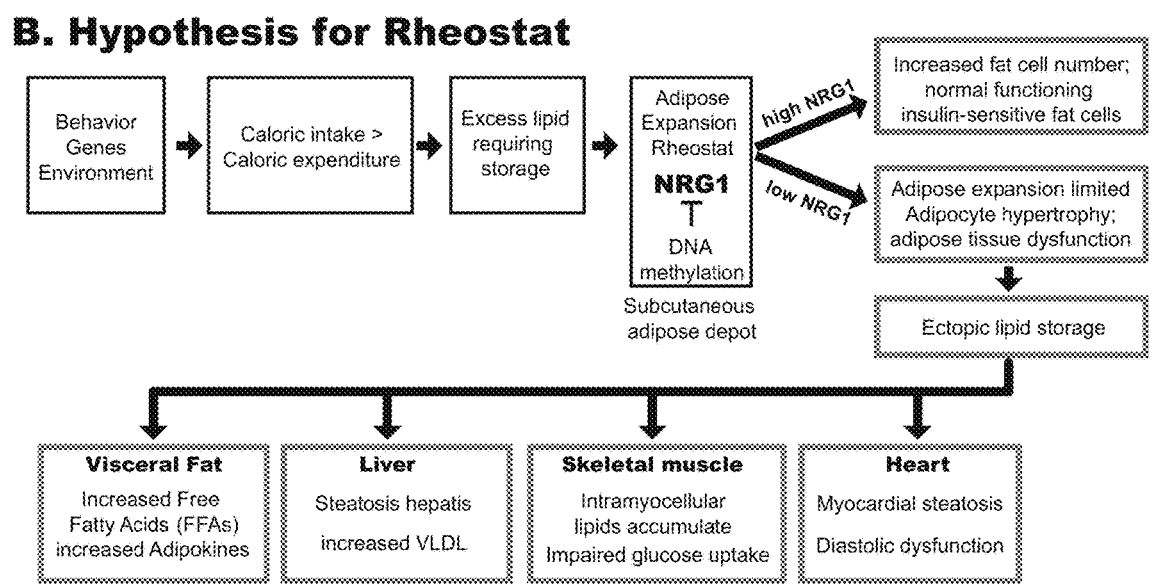
FIG. 1B shows the model of ectopic lipid accumulation and consequences, and the role for Neuregulin-1 (NRG1) in promoting adipose stem cell differentiation, and promoting healthy fat (green box) as opposed to unhealthy (red boxes).
Figure 2:
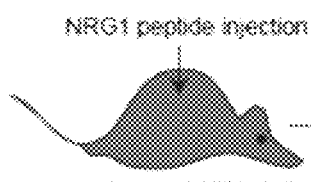
FIG. 2 shows the model based on the described findings. A. Identification of NRG1 as a driver of adipose differentiation in vitro. B. Published results from mouse showed injected NRG1 causes weight loss and leptin increase in vivo. C. Model proposed to explain these results. D. Proposed in vivo test of the model (See examples). E. Proposed locating the epigenetic control point of NRG1 (See examples). F. Proposed identifying the NRG1 receptor in adipocytes (See examples).

The present finding of NRG1 as a novel driver of adipose expansion has significant clinical impact for therapy of obesity: wild-type mice treated with injections of recombinant NRG1 display lower bodyweight and reduced percent body fat relative to controls, and in an obese mouse model, greater metabolic health via improved glucose tolerance. Hamsters also showed weight loss on NRG1 administration. Based on the present model, NRG1 will be an excellent therapeutic for reversing obesity-related disease and may lead to weight loss depending on how the leptin feedback loop is activated in humans (FIG. 2C).

Interestingly, NRG1 has already been successfully tested in clinical trials for heart failure, so it is safe in humans (no effect on bodyweight was noted in those studies but they may have been too brief, 10-11 days, whereas the mouse studies took 8 weeks). Remarkably, though multiple studies of recombinant NRG1 in rodents, all of which demonstrated positive metabolic effects, no previous study examined adipose expansion directly, leaving a critical gap in our knowledge. This is even more surprising given that NRG1 caused a dramatic spike in leptin, an adipocyte-secreted hormone.

Figure 7:
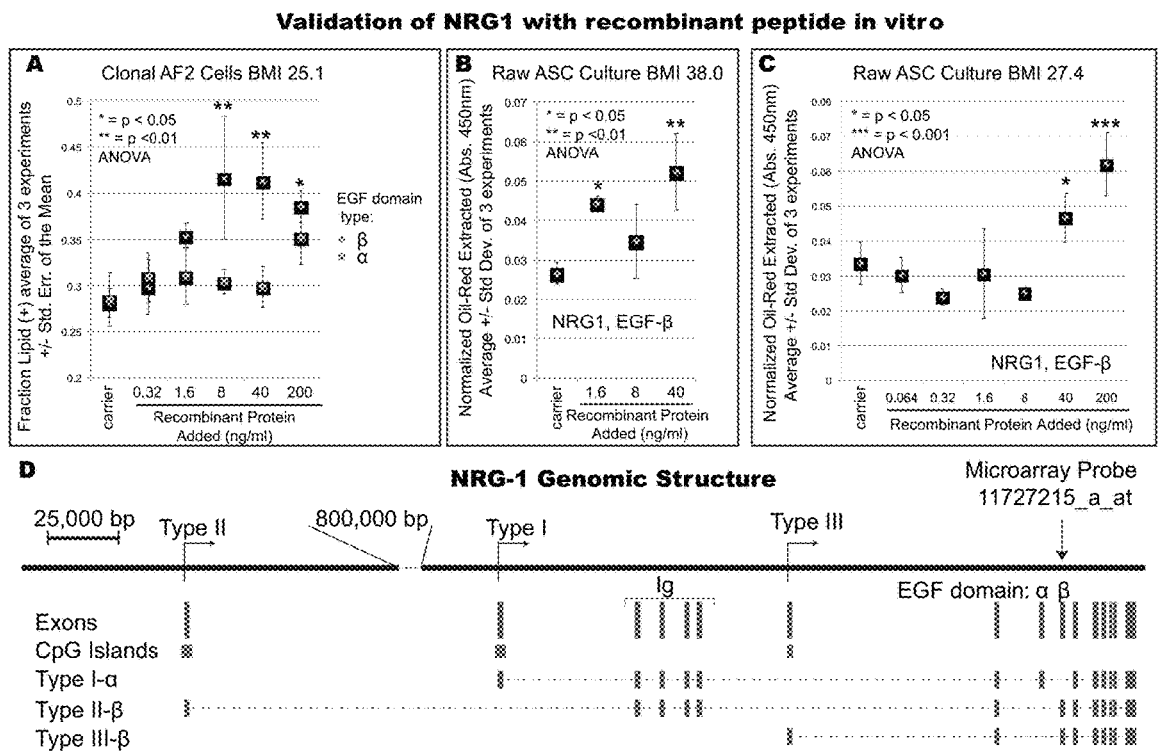
FIG. 7 shows the validation of NRG1 in vitro and genomic structure of the NRG1 locus. A. Recombinant NRG1 added to the culture media recapitulates the effect of DAC in AF2 clonal cells. Only the beta isoform shows activity. B. Second validation with recombinant NRG1 in raw ASC cultures (BMI=38.0). C. Third validation of recombinant NRG1 in raw ASC cultures (BMI=27.4). Asterisks represent p-values of 1-way ANOVA relative to the carrier control. D. Genomic structure of NRG-1. Note that microarray probe 11727215_a_at lies within the EGF-β exon, while the EGF-β peptide showed activity in panels A-C. Types I-III are alternative transcription start sites.

We observed that an epigenetic drug (decitabine, DAC) causes greater differentiation of adipose-derived stem cells (ASCs) in vitro (FIGS. 7A,B,C). We have also demonstrated that the observed increases in differentiation represent differentiation vs stem cell fate choices, not partial differentiation phenotypes.

First discovered in 2001 by Patricia Zuk and co-workers, ASCs are isolated from lipoaspirates and have proven to be useful in obesity research since they can be induced to differentiate into multiple lineages, including adipose, in vitro. Adipose differentiation in these cells involves a very well characterized pathway including transcription factors PPARγ and C/EBPα, and activation of Bone Morphogenetic Protein (BMP) signaling concomitant with inhibition of Wnt signaling. There have been a number of studies of epigenetic changes during ASC differentiation. The consensus in the field is that significant methylation changes do not drive differentiation of these cells but rather epigenetic programming is established in the stem cell lineage in vivo prior to isolation from a patient. Therefore, the interesting question is what epigenetic mechanism is programmed into the stem cells to control their adipose differentiation ability. We had sought to address this question. By focusing on the process of differentiation itself, previous studies did not address the control of differentiation efficiency, which was our goal, and which led us to construct our studies differently than previous work. Instead of measuring methylation and gene expression during differentiation, we performed epigenetic reprogramming and gene expression analysis in stem cells. We view adipose differentiation as the readout of stem cells' epigenetic status, correlating differentiation efficiency with gene expression in stem cells (FIG. 6D). This approach has enabled us to make significant progress as outlined below.

Brown Adipose Tissue (BAT) and Neuregulins. The adipose biology field has recently been galvanized by the re-discovery (in adults) of brown adipose tissue (BAT): a thermogenic, energy-expending cell type, and the related beige/brite (brown-in-white) cell types. There is much excitement about the possibility of treating obesity by promoting 'browning' of white adipose tissue (WAT) to induce metabolically beneficial outcomes.

One recent study showed that acetylcholine, produced by immune cells, acts on white adipocytes to promote their browning. Interestingly, Neuregulin-4 (NRG4) is a brown adipose marker, identified by transcriptomic analysis of 'browned' fat, and may function as an adipokine signal from BAT to neurons. Recently, overexpressing NRG4 was shown to prevent diet-induced obesity in mice, and to promote metabolically favorable outcomes. While we find NRG4 is expressed at low levels in our in vitro primary human WAT stem cell culture, NRG1 is more highly expressed (FIG. 3A), and epigenetically inducible (FIGS. 3D, E) and we show it is the WAT equivalent to NRG4 in BAT. Thus, our work adds a critical piece of the neuregulin and fat picture for WAT. Expression and epigenetic modulation of NRG1 in WAT (FIG. 3) suggests it plays a previously unknown, but important, role in adipose biology.

The ability to inactivate a gene in a depot-specific manner in vivo and expose the mice to a high-fat diet, driving adipose tissue expansion, provides a powerful opportunity to evaluate the regulatory role of NRG1 in fat biology. NRG1 is robustly expressed in murine adipose precursor cells derived from inguinal and perigonadal depots, and at higher levels than in human ASCs (FIGS. 3B, C, compare to FIG. 3A). We conclude NRG1 is expressed in the tissue of interest and is therefore a suitable target of inactivation. It is our hypothesis that NRG1 expressed within the resident mouse adipose precursor population directly establishes the expandability of that fat pad.

Our model for NRG1 function in adipose tissue is shown in FIG. 2C and key aspects of the model are shown in FIGS. 2D, E, F. The model can be summarized as follows: NRG1 is an epigenetically regulated (FIGS. 3D, E) molecular rheostat establishing the level of differentiation of WAT stem cells, ensuring that competing goals are met: long-term stem cell maintenance, and on-demand adipose expansion by hyperplasy. As a positive regulator of adipocyte differentiation (FIGS. 7A,B,C), NRG1 indirectly affects leptin levels, leading to effects on bodyweight through anorexigenic signaling in the hypothalamus. In this model NRG1 functions in an autocrine or paracrine manner to regulate stem cell behavior within WAT itself (FIG. 2F), but also has an indirect role in WAT-to-brain signaling (FIG. 2C), a role analogous to NRG4 in BAT, which serves directly as a secreted signal to the brain.

This model is supported by multiple lines of evidence both in vitro and also in vivo (mouse, rat and hamster injection experiments from other laboratories). Several reports have been published of the effects of NRG1 injections into mouse and rat but has not directly examined the effect on adipose tissue in any of them. However, these in vivo data are entirely consistent with our model (FIG. 2C).

Most strikingly, after 8 weeks of NRG1 administration in wild-type mice, leptin levels were elevated over 6-fold; leptin is predominantly secreted from adipose tissue, agreeing with the present findings that some expansion of adipose depots occurred. Leptin is secreted more from subcutaneous depots than visceral, suggesting that NRG1 may specifically promote expansion of healthy fat. NRG1-treated mice weighed less than control animals at the end of the experiment but that is because NRG1 blocked normal weight gain rather than causing weight loss; the treated animal's weight remained steady rather than increasing with time as is occurs even on chow diets. This effect of NRG1 on bodyweight is clearly due to leptin signaling because it was blocked in db/db leptin-receptor mutant mice. Therefore, we show and conclude that the direct role of NRG1 is the hyperplasia of subcutaneous adipocytes while the secondary effect is increased leptin signaling, ultimately resulting in bodyweight differences (FIG. 2C). While no weight difference was observed in control vs. NRG1 treated db/db mutant mice, their glucose tolerance improved, similar to the reversal of diabetes induced by adipose expansion in the 'metabolically healthy obese' ob/ob mouse. Previous studies also reported improved glucose tolerance in rats as a result of NRG1 injection. As noted in the background section, increased adipose tissue can be metabolically beneficial, as long as it is the right type of adipose tissue: subcutaneous rather than visceral, and hyperplastic rather than hypertrophic. Therefore, our present model and data shows that the NRG1-injected rodents experienced an expansion (hyperplasia) of subcutaneous adipose depots leading to improved metabolic health and increased leptin secretion, ultimately affecting their bodyweight.

As described above, fifteen years ago it was found that stem cells, termed Adipose-derived Stem Cells (ASCs), could be obtained from lipoaspirates (liposuction fat), and they are capable of subsequent differentiation in vitro into mature adipocytes (fat cells), as well as chondrocytes (cartilage), osteoblasts (bone) and myocytes (muscle). The process of differentiation simply requires specific cocktails of hormones added to the cell culture media. This finding opens unprecedented opportunities for investigating regenerative medicine in primary cell culture, and gives the researcher exquisite control over the differentiation process in vitro. While transformed mouse cell lines C3H10T1/263 and 3T3-L164,65 have established a molecular paradigm for adipose differentiation, primary human cell lines are derived from actual patients and are derived from the obesity-relevant subcutaneous adipose depot, while maintaining multilineage differentiation capacity. Using these cells, we have recently identified and published results describing a novel quiescent stem cell fate. Building on these results, we describe the discovery of NRG1 as a mediator of adipose differentiation-vs-quiescent stem cell fates. As a regulator of adipose differentiation in vitro, we propose NRG1 performs the same role in vivo. In future studies, we also aim to leverage the powerful primary cell culture model system to shed light on both the epigenetic mechanism of NRG1 regulation and also the mechanism by which NRG1's signal is transduced by stem cells in making differentiation-vs-quiescence fate choices (See examples below).

Because patient-derived cells, such as ASCs, are highly heterogeneous, it is vital to ensure that the differences in cell behavior are truly fate decisions and not a measure of non-stem cell contamination (perhaps immune cells, fibroblasts, or other cells). We therefore have performed our experiments with clonally-derived cells expanded in the inventor's laboratory. Many of our experiments use a single clonal line isolated from ASC080414A (Zen-Bio, Inc.), called the AF2 line. Clonal isolation has the advantage of minimizing both genetic and epigenetic variance, which enabled us to identify a highly significant signal in our data (FIG. 6E). After identifying NRG1 and confirming its driver role in vitro with AF2 cells, (FIG. 7A) we replicated the results in 'raw' lipoaspirate-derived ASC culture to verify the effect is general to more than one cell line or one patient (FIGS. 7B, C).

Figure 4:
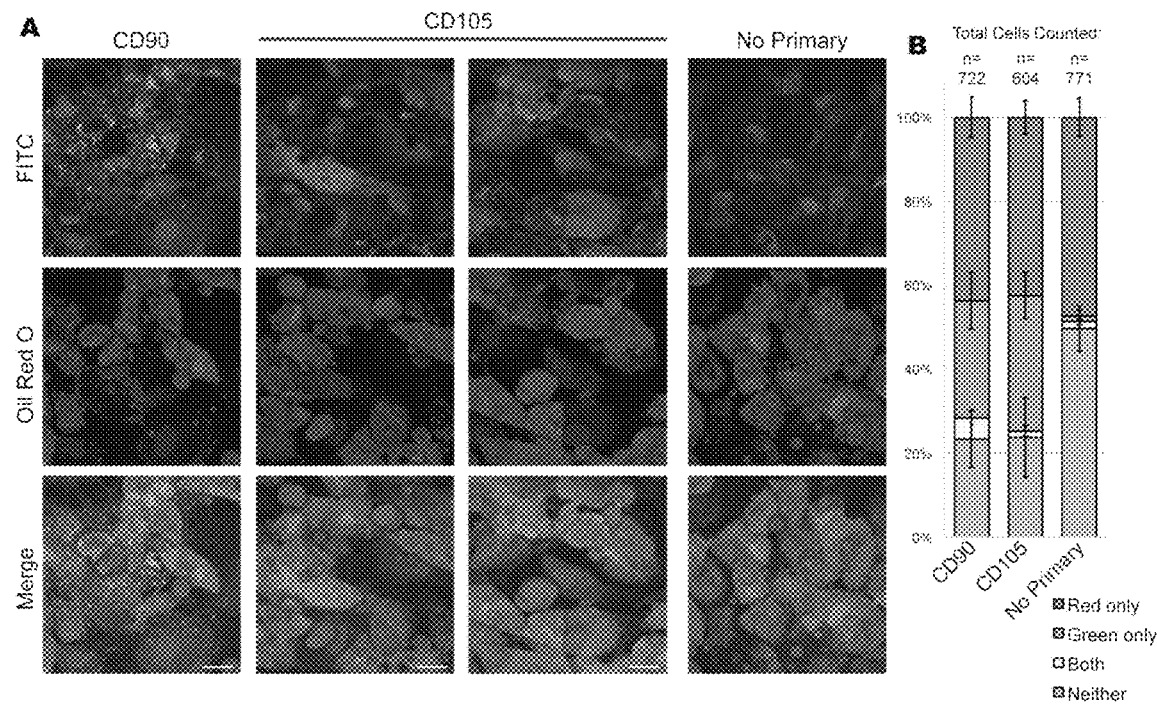
FIG. 4 shows identification of a differentiation-resistant stem-like cell population. CD90 and CD105 surface markers are detected by immunofluorescence in differentiated cell line ASC021606 (BMI=32.1). A. Cells were fixed and stained with FITC signal (green) for surface markers and counterstained with Oil Red O for lipid content. All panels represent compressed Z-stacks taken and displayed under identical conditions. Scale bars=20 µm. C. Quantitation of green and red cells observed after CD90 or CD105 immunofluorescence with Oil Red O staining. Data represent the average and standard deviation of three fields.
Figure 5:
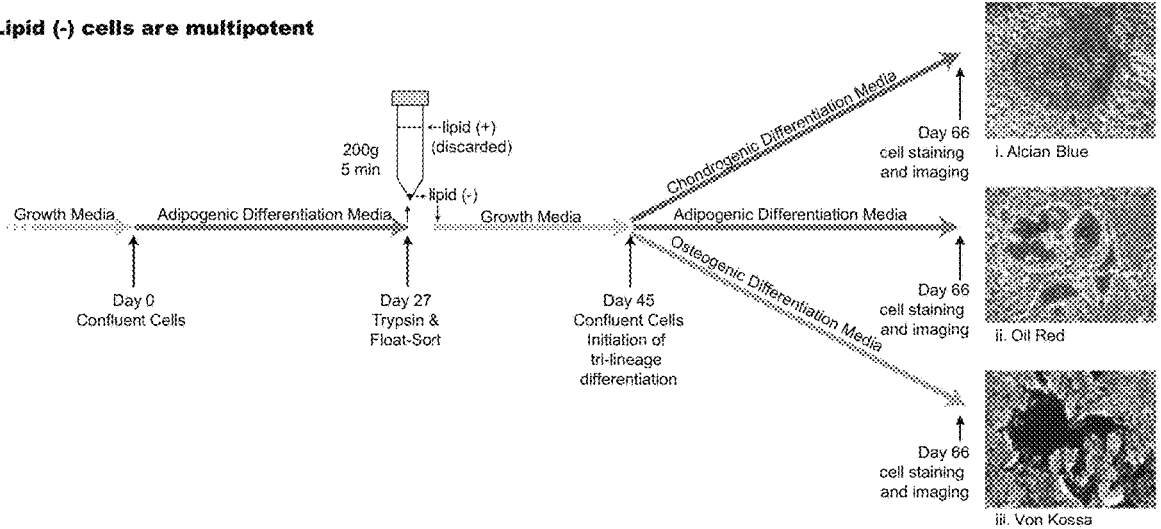
FIG. 5 shows that lipid (−) cells are multipotent. Clonal AF2 cells used. After one round of adipogenic differentiation we float-separated the lipid (−) population and re-grew to confluency before tri-lineage differentiation and staining for (i) cartilage, (ii) fat, and (iii) bone. (See Paffhausen et al., 2018).

Quiescent stem cells have been reported in skin, gut, blood and neurons, but have yet to be defined in adipose tissue. Intrigued by the undifferentiated (or lipid(−), lacking in lipid) remaining in adipose culture after adipose differentiation, we performed cell surface marker staining with the stem cell markers defined by the International Society for Cell Therapy, finding that both CD90 and CD105 signal were retained on the lipid(−) cells after adipose differentiation (FIG. 4). We were able to differentiate ASCs (the AF2 clonal line) for 27 days into adipose lineages, recover replicative lipid(−) cells by float-sorting, grow them to confluence, and then perform tri-lineage differentiation in bone, cartilage, and fat (FIG. 5). Therefore, even after 27 days of adipose differentiation bona fide multipotent stem cells remain in culture and can be reawakened to growth and differentiation as needed. This finding was critical to enable us to interpret the results of epigenetic drug treatment, which increases the differentiation of adipocytes (lipid-positive) at the expense of the lipid(−) stem cell reservoir—in other words, it shifts the cells towards a differentiated cell fate (FIGS. 6A,B,C).

The drug decitabine (5-aza-2'-deoxycitidine, or DAC) is an effective, genome-wide DNA methylation inhibitor that can be added directly to the cell culture media. This drug has previously been shown to alter adipose differentiation efficiency in human ASC culture, both in the literature and the inventor's laboratory (FIGS. 6A,B,C), but the mechanism remains unknown. DAC is a non-specific demethylating agent, so the whole genome will be affected and potentially large numbers of gene expression changes should be expected. The challenge was to identify 'driver' gene expression changes, not 'passengers' that are epigenetically changed but not functionally important.

First, by evaluating gene expression in stem cells immediately after DAC treatments (rather than differentiated cells), we minimized secondary gene expression changes caused by the differentiation process itself. Second, hypothesizing that the expression of driver genes will more strongly correlate with differentiation efficiency than passenger genes, we obtained the Pearson's correlation between candidate gene expression in stem cells and the relative formation of adipocytes after 14-18 days of adipogenic induction. Third, we used a clonal cell line (AF2) in order to minimize epigenetic variability between cells. We performed DAC treatment at two concentrations, relatively low (0.125 µM) and high (1 µM) along with a DMSO-only (untreated) control (FIG. 6C).

The single most statistically DAC-upregulated probe (FIG. 6E) is 11727215_a_at is located within the Neuregulin-1 (NRG1) gene (FIG. 7D). However, other probes showed a stronger fold-change, though lacking the statistical reproducibility of NRG1 (FIG. 6E). Of the 22 probes with over 4-fold expression change (and p-value<0.05 by ANOVA), 11 are distinct genes (Table 1). However, these highly DAC-induced genes are not, in general, good candidates for differentiation drivers: for example, eight different Keratin-8 probes are in the list, yet this intermediate-filament protein is unlikely to drive differentiation differences.

Interestingly, the two genes higher than NRG1 in Table 1, Keratin-8 (KRT8) and Metallothionein 1G (MT1G) are known to be epigenetically regulated in cancer cell lines, specifically through DNA methylation of their promoters. Therefore, we regard the strongly upregulated genes as 'endogenous epigenetic reporters', giving an indication that the DAC treatment was working correctly.

From the upregulated gene list NRG1 is the most intriguing as a potential driver of adipose differentiation: it is well known to regulate stem cell differentiation in brain and heart. However additional lines of evidence make this an intriguing finding. As noted, there was extremely high statistical confidence in this probe (high reproducibility in induction on DAC) (FIGS. 6C, D, E). We also found extremely good Pearson's correlation (0.993) between the NRG1 expression and adipose differentiation (FIG. 6D). By RT-qPCR validation, we identified a specific isoform of NRG1 that was more robustly induced (~10 fold, FIG. 3, FIG. 6E). RT-qPCR analysis showed that one NRG1 isoform was approximately 10-fold up-regulated on 1 µM DAC relative to DMSO control (FIG. 3, FIG. 6E), leading us to the conclusion that the microarray readout captured multiple isoforms, at least one of which (Type I) exhibits a mild ~2-fold increase, and likely constituted the majority of signal detected by microarray (FIG. 3, FIG. 6E).

NRG1 is known to signal through its Epidermal Growth Factor-like (EGF-like) domain, where it ligands with the ErbB family tyrosine kinase receptors (usually ErbB3 or ErbB4). There are two alternative isoforms of the NRG1 EGF-like domain, α and β, encoded on alternatively used exons. Because it is well studied, there are commercially available NRG1 recombinant peptides available. We obtained one of each isoform I-VI from BioLegend (Cat #711104, EGF-β and 559502, EGF-α) and tested them in our differentiation assay with AF2 cells. The NRG1 EGF-β peptide, having SEQ ID NO: 1 (SHLVK-CAEKEKTFCVNGGECFMVKDLSNPSRYLCKCP-NEFTGDRCQNYVMASFY KHLGIEFMEAE) was able to recapitulate the differentiation induction observed with DAC and EGF-α was inactive (FIG. 7A). Remarkably, the upregulated microarray probe (11727215_a_at) overlaps the EGF β-type domain specifically (FIG. 7D). We went on to validate two other 'raw' lipoaspirate cultures, confirming that NRG1's role is not limited to the AF2 line or a specific donor (FIGS. 7A,B,C).

Blood contains detectable but variable levels of circulating NRG1-β: from around 2.6-4.1 ng/ml in one study of coronary artery disease to 32 ng/ml-473 ng/ml in a study of cardiovascular fitness; these encompass the range in which we observed activity in vitro (FIGS. 7A,B,C). Consistent with the variability between studies and patients, we observed significant cell-to-cell variability in NRG1 sensitivity, which may have to do with clonal vs. raw ASC preps or with donor body mass index (BMI). In cell culture, we tested the EGF-like domain only (SEQ ID NO: 1; 65 amino acids, or about 7 kDa), while circulating NRG1-β is about 40 kDa, so correction of peptide concentrations by a factor of 6 (the ratio of molecular weights) gives a predicted full-length 'active' concentration equivalent of 9.6 (1.6×6) ng/ml to 1,200 (200×6) ng/ml, overlapping the physiological 2.6-473 ng/ml range.

Figure 3:
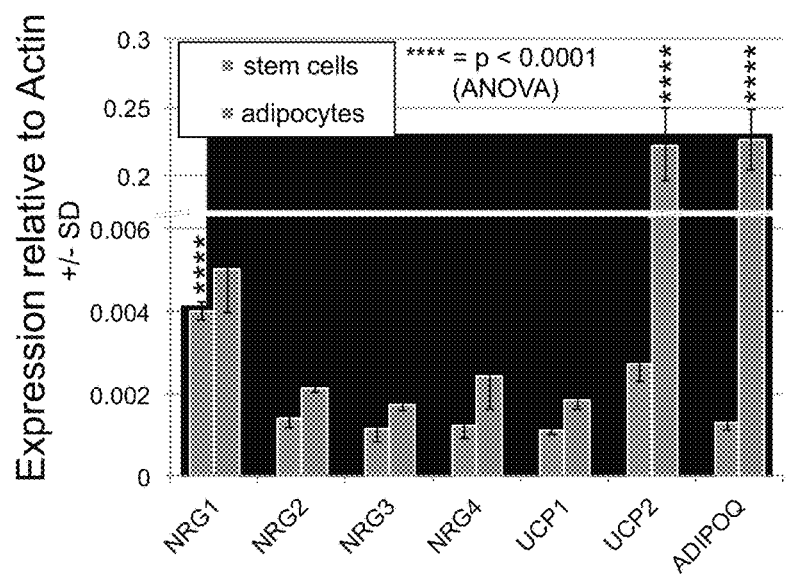
FIG. 3 shows expression and induction of NRG1 in WAT adipocytes and adipose stem cells. A. Microarray data showing that NRG1 is preferentially expressed in clonal cell line AF2, both stem cells and adipocytes. UCP1 is a brown adipose tissue (BAT) marker and UCP2 is a white adipose tissue (WAT) marker. Adiponectin (ADIPOQ) shown as a differentiation control. P-values calculated relative to NRG4 using 1-way ANOVA. Analysis of gene expression in mouse adipose precursor cell lines isolated from inguinal (B) or perigonadal (C) depots of a male mouse. ANOVA analysis followed by Tukey's HSD post-hoc test reveals that NRG1 expression is significantly different (p<<0.01) from all other genes in both A and B. Microarray data from Lee et al., 2019. NRG, Neuregulin; UCP, uncoupling protein; AdipoQ, adiponectin. Isoform-specific epigenetic induction of NRG1 expression in primary human cells, clonal (D) and raw processed lipoaspirate (E). Expression of NRG1 is induced with demethylating agent decitabine (DAC). Types I-III represent distinct transcriptional start sites within the NRG1 locus and produce different mRNA isoforms (see FIG. 7D for map). The Type III isoform is specifically DAC responsive. P-values derived from Tukey's HSD post-hoc test after ANOVA and are relative to corresponding matched DMSO control. Note Type II isoform expression was not detected in the stem cells.
Figure 3:
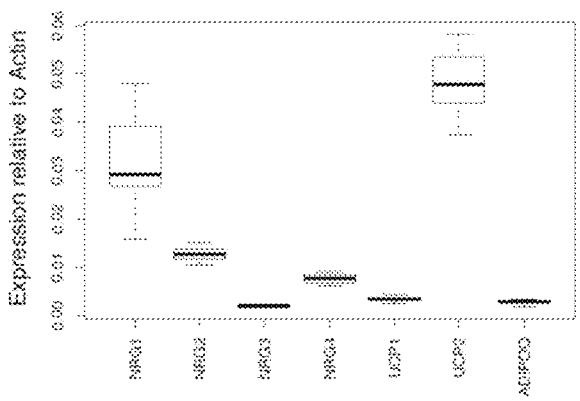
Figure 3:
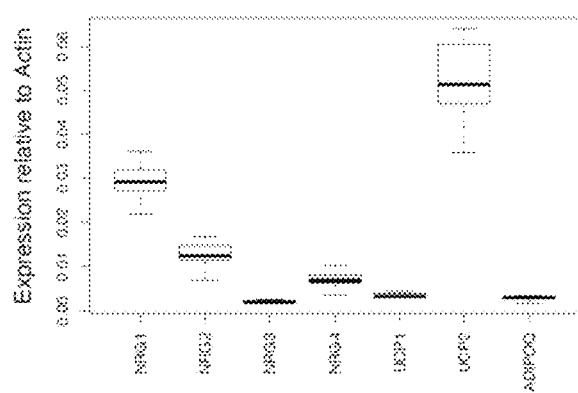
Figure 6:
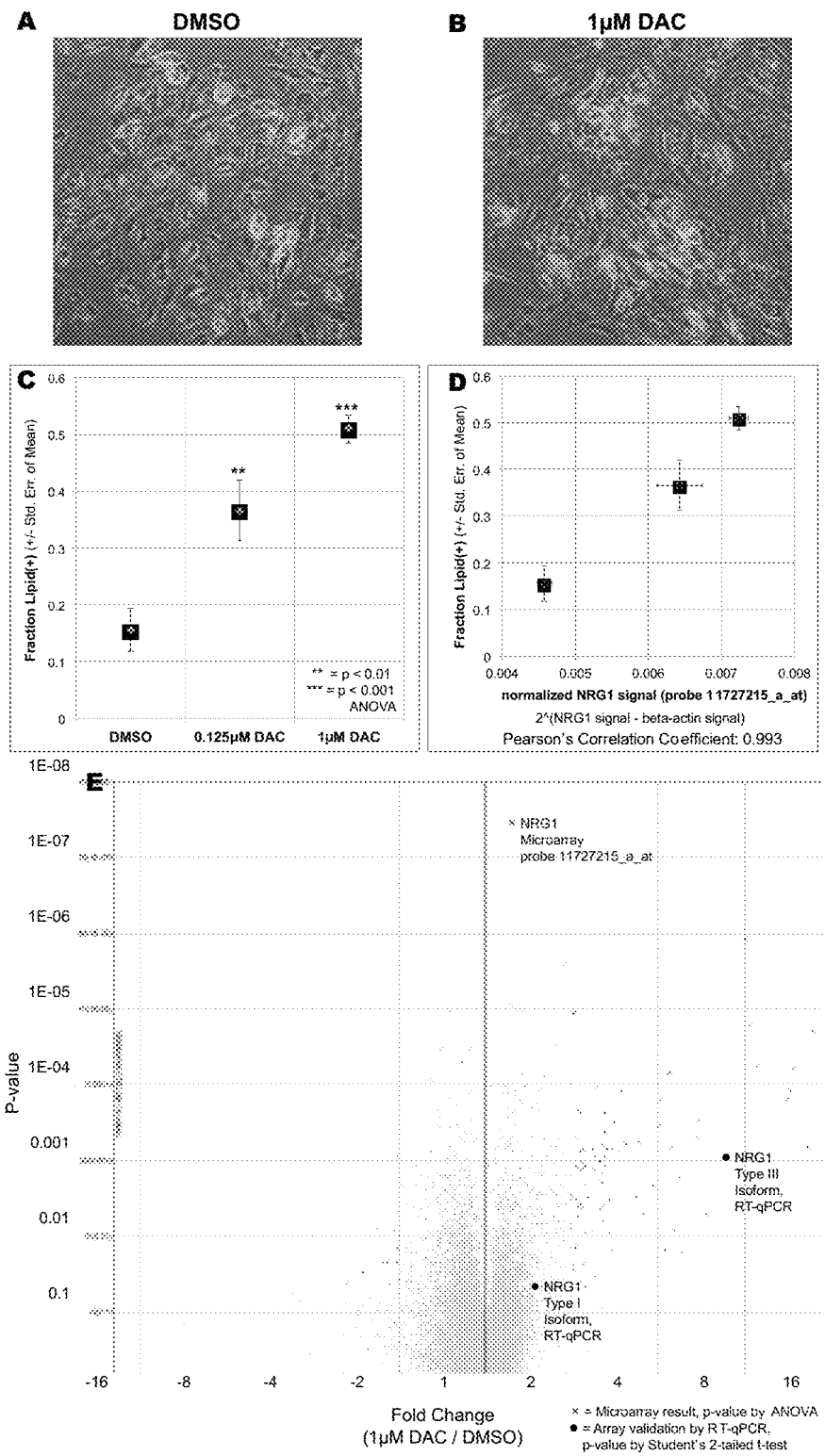
FIG. 6 shows the discovery of NRG1 as an epigenetically regulated gene in adipose stem cells. A. Image of DMSO (control)-treated AF2 cells after differentiation into adipocytes. Accumulated lipid is a straw color on the purple background. B. DAC-treated stem cells were differentiated and show increased lipid-positive cells. C. Quantitation showing DAC causes increased differentiation. All experiments performed as three biological replicates, with error bars showing S.E.M. D. The NRG1 microarray probe (11727215_a_at) correlates positively with differentiation (Pearson's correlation coefficient 0.993). E. Volcano plot of microarray data, 1.0 µM DAC vs. DMSO. Validation by RT-qPCR shown on volcano plot as filled circles at appropriate fold-change and p-value (Two-tailed Student's t-test). Note NRG1 isoform II was undetected by RT-qPCR.
Figure 8:
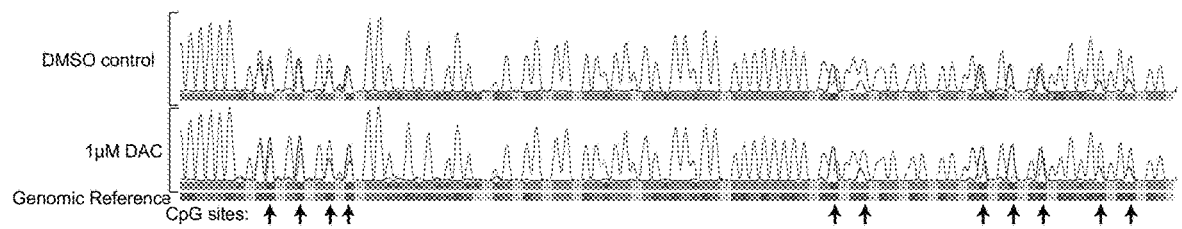
FIG. 8 shows bisulfite-PCR of Type III CpG island. Bisulfite treatment causes cytosine (C, blue) to sequence as thymidine (T, green). Methylation is detected as retention of cytosine (blue traces) relative to T (green traces) on chromatograms (for clarity, G and A traces omitted). Note that 1 µM DAC does not demethylate this locus. Arrows mark CpG sites where methylation can occur.

While our experiments match physiological concentrations in blood, we identified Type III isoform of NRG1-β as DAC-induced within stem cells, not blood (FIG. 3, FIG. 6E). Instead, this isoform is membrane bound, and ideally suited to participate in extremely close cell-to-cell juxtacrine interactions where effective concentrations may be locally very high. The strong DAC-responsiveness of NRG1 type III isoform expression (FIG. 3, FIG. 6E) prompted bisulfite-PCR examination of its associated CpG island (FIG. 7D) which is only 240 bp long and encodes 16 CpG motifs. In FIG. 8, we show the results for eleven of these CpG motifs, from the exact same experiment shown in FIG. 3 and FIG. 6. (We isolated both RNA and DNA from cells using Zymo Research Quick DNA/RNA Kit). While methylation could be seen in the DMSO control, it was not decreased upon treatment with 1 µM DAC, and if anything, the methylation increased after treatment (FIG. 8), and yet we know that significant NRG1 expression change occurred (FIG. 3B). The most straightforward explanation of this result is that methylation changes happening elsewhere in the genome are regulating the Type III isoform of NRG1 (and more strongly than other isoforms, see FIG. 3B).

Here, we have shown that epigenetic control of Neuregulin-1 (NRG1) affects adipose differentiation of stem cells in vitro. Building on this finding, we established a model in which NRG1 is a WAT specific regulator analogous to the role of NRG4 in BAT. Specifically, we hypothesize that NRG1 functions in a paracrine or autocrine manner to regulate formation of new adipocytes from stem populations, both in vitro and in vivo. In neurons, NRG1 has been shown already to play a similar role, promoting neuronal cell differentiation from progenitors in the vertebrate cortex and retina and even promoting neuronal differentiation in vitro. Similarly, in the heart, NRG1 promotes differentiation of cardiomyocytes from their stem cell progenitors both in vivo and in vitro and for this reason has been successfully tested in clinical trials for heart failure. Our model (FIG. 2C) extends these findings to adipose biology. We propose that the epigenetic control of NRG1 may constitute an intrinsic mechanism limiting the expansion of WAT depots, potentially elucidating important health implications for the comorbidities of obesity.

EXAMPLES

Example 1

We will follow an established protocol to perform chronic administration of NRG1 peptide (SEQ ID NO: 1; a short EGF-beta domain peptide we used in FIGS. 7A,B,C) by injection into the peritoneum (50 µg/kg) three times per week for 8 weeks using wildtype (C57BL/6JRj) mice. We will assess adipose expansion in various depots and effects on stem-cell differentiation. Because the C57BL/6JRj mouse is resistant to diet induced obesity (DIO), we will perform a second study in which we use the related C57BL/6J genetic background under both lean and DIO conditions, for the first time assessing NRG1's role in a relevant model of common human (diet-induced) obesity.

We will use 16 male mice (no females), n=8 in each treatment group (vehicle or NRG1 injection) and inject the mice with NRG1 at 50 µg/kg bodyweight, 3×/week, for 8 weeks. Our analysis of previous results suggests that, based upon the large change in bodyweights at the end of the study and the small variability observed, 4 mice would enable detection to p<0.05 with a power of 90% (0.90). We will also use n=5 males and n=5 females in either vehicle or treatment groups, (n=20 total mice). Thus we will control for sex as a biological variable while maintaining statistically robust group sizes, with fewer mice per group.

We will assess bodyweight weekly and final circulating leptin and insulin levels after 8 weeks. We will also assess glucose clearance at the 8-week endpoint, and we will assess body fat vs. lean mass by NMR at 8 weeks. We will assess adipose expansion directly at 8 weeks by euthanizing the mice, dissecting out the inguinal (subcutaneous), mesenteric (visceral), and interscapular (BAT) fat pads. By measuring fat depot weight, and histologically analyzing adipose size and numbers, we can estimate total adipocyte numbers, adipocyte size distribution (hypertrophy vs hyperplasia) and the relative changes in fat distribution induced by chronic NRG1 treatment. Parlee et al. 2014 provide a detailed protocol for the dissection of fat depots followed by formalin and ethanol preservation and histology with semi-automated counting of adipocyte size and numbers using Image J. A recent study in rats fed dietary flavonoids successfully used this method to document a shift from hypertrophic to hyperplastic obesity. Therefore we will follow these protocols to examine adipose expansion in NRG1-treated mice, hypothesizing that NRG1 will induce the expansion of subcutaneous (inguinal) depots. This model is supported by the demonstrated effect of NRG1 on leptin secretion and leptin's greater expression from subcutaneous than visceral depots. Importantly, by also measuring interscapular fat pads we will assess any effect of NRG1 on brown adipose tissue expansion or adipocyte size for the first time. From three mice per group, we will save half of the inguinal fat pads for ASC isolation.

The portion of the murine inguinal fat pad not used for histology (above) will be used for ASC extraction. Protocols for ASC isolation from mouse adipose depots have been described in detail and are similar to the human ASC isolation: collagenase treatment to disassociate the tissue followed by plating and multiple wash steps to remove contaminating blood and other non-adherent cell types. The cells are grown in 5% $CO_2$ atmosphere in DMEM media to promote ASC propagation. We will confirm expression of CD105, CD73, and CD90 by immunofluorescence (FIG. 4) and/or FACS. We then will perform in vitro cell culture and differentiation into adipocytes to test whether cells exposed to NRG1 in vivo show differentiation increases as we observed for human cells (FIGS. 7A,B,C). To keep the number of cell lines manageable, we will isolate cell lines only from inguinal fat pads and from three mice per treatment group. The logic of the experiment is quite similar to our studies of human adipose-derived stem cells except the NRG1 exposure will occur in vivo. The differentiation assays will be carried out identically to our previous studies (FIGS. 7A,B,C).

This example will use the C57BL/6J background, a commonly used mouse model of diet-induced obesity. Given the variability of DIO induction, we will test n=8 mice per group, divided into high-fat diet vs. chow, while also dividing into male vs. female and NRG-1 vs. vehicle injections (n=64 mice in 8 groups). We will also measure food consumption and energy expenditure.

Given the literature showing effects of NRG1 on mouse, rat, and hamster physiology, NRG1 should have an effect; the question is whether adipose depots sizes will be altered. If no effect is observed at the three depots described above, we will widen the examination to include retroperitoneal and epididymal depots, expanding to cervical, axillary, mediastinal, perirenal, perivesical, and omental depots as necessary. If leptin remains unchanged, but bodyweight changes, we will examine muscle physiology, since NRG1-mediated increases in skeletal muscle respiration were reported in another study.

Example 2

Determining the epigenetic control locus modulating NRG1 expression. The epigenetics field has long been hobbled by observed epigenetic changes which do not match altered gene expression patterns: epigenetic changes are often seen far from genes, or gene expression changes occur far from differentially-methylated regions. The functional implications of these 'correlative' data are not clear. Here we propose that chromatin conformation may be the 'missing link' between epigenetic and gene expression changes. Somewhat analogously to a folded protein, the genome as a whole has a structure that is central to its function. Loops of DNA bring distant regulatory elements together with promoters to initiate transcription. Thus, enhancer elements can be tens or hundreds of thousands of base pairs away from their regulatory targets in genomic space, yet be proximal in genome 3D space. Entirely separate chromosomes can contact each other to bring critical regulatory regions together. Fortunately, recent advances in chromatin studies provide tools that capture this chromosomal conformation, and we will apply these techniques in primary human ASCs to identify candidate regulatory regions contacting NRG1.

In addition to linking epigenetic with gene expression changes, we would like to determine whether chromatin structure brings epigenetic control regions near to NRG1, or whether epigenetic changes alter the structure of the genome such that NRG1 expression is changed. One outcome is that NRG1 interacting regions are relatively unaffected by DAC, leading us to conclude that the structure simply brings epigenetic control regions near to the NRG1 promoter. Another potential outcome is that both DNA methylation and chromatin structure are altered together with NRG1 expression. By jointly examining DNA methylation and NRG1 interacting regions in control and DAC-treated stem cells, we can determine the real functional changes. We will be the first to explicitly explore the functional relationship of changing (by DAC) DNA methylation on chromatin conformation and cell differentiation in primary human stem cells.

Methylation. To identify strongly demethylated regions in our DAC-treated cells, we will examine methylation genome-wide using the Infinium MethylationEPIC BeadChip, which measures methylation at over 850,000 sites per sample. This technology provides genome-wide epigenetic data that can be compared in DMSO and DAC-treated cells.

Chromatin Conformation. Using Circular Chromatin Conformation Capture (4Cseq), we will examine the interaction between a region of interest (the 'viewpoint' where primers are designed) with more distal regions genome-wide. This technique has been used in hundreds of studies including evaluation of interactions with the H19 imprinting control locus, the HoxB1 gene, olfactory receptors, and the insulin promoter, among many others. Detailed experimental protocols and data analysis pipelines are available. By superimposing the methylation maps (from the Infinium MethylationEPIC Chip) with Neuregulin-1 interaction maps (from 4C-seq), we will identify candidate regions of epigenetic regulation of NRG1. As described below, we will then perform the critical functional test: manipulation of methylation at the candidate locus followed by measuring expression of the NRG1 Type III isoform and differentiation into adipocytes. Alternative strategies. There are several alternative strategies to 4C-seq that we can use: chromosomal interaction capture (T2C) uses a microarray-based capture method rather than circularization, and Hi-C-seq surveys an all-vs-all genome-wide interaction network.

Figure 9:
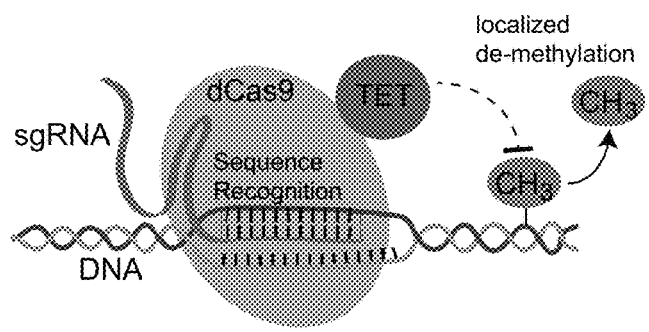
FIG. 9 shows a schematic for functionally testing epigenetic modifications using programmable DNA demethylation. CRISPRdCas9-TET is targeted using the single guide RNA (sgRNA, green), which allows dCas9 to target a specific sequence. The attached TET moiety then locally demethylates DNA (methyl group, CH3, orange.).

Epigenetic Validation by CRISPR. The discovery of Clustered Regularly Interspaced Short Palindromic Repeat (CRISPR), a programmable genome-editing system, has revolutionized genomic research. Originally described as a custom targetable molecular scissors, the technology has been adapted in myriad ways. For example, deactivated Cas9 nuclease (or dCas9) is a platform for protein fusions, making them targetable. CRISPR-TET (TET is a DNA demethylase enzyme) enables localized demethylation of DNA. Using the CRISPR-TET system, localized DNA demethylation can be programmed by introducing a 'single guide RNA', or sgRNA, which targets the dCas9-TET construct to precise genomic locations (FIG. 9). Our validation will be to target the candidate control region of NRG1 for demethylation. Based on our model, this should cause increased differentiation in our primary cell culture while also increasing NRG1 Type III isoform expression.

Alternative Strategies. In mammals, the deposition of DNA methylation is guided by a DNA Methyltransferase (Dnmt) family of proteins, of which 3 members act on DNA: Dnmtl, Dnmt3A, and Dnmt3B. Recently, three groups produced a dCas9-DNA Methyltransferase 3A protein (dCas9-Dnmt3A) and demonstrated that it gives the ability to program localized DNA methylation. Therefore, we will use a dCas9-Dnmt3A construct as an alternative strategy if the dCas9-TET fusion fails. Importantly, we anticipate the direction of action will be inverse to the TET fusion: we'd predict differentiation should decrease, not increase. There are also other epigenetic approaches that can be used: DNA methylation is only one aspect of epigenetic control. Another mechanism operates via the post-translational modifications of histones: proteins around which DNA is wrapped and that carry epigenetic information. One way they carry epigenetic information is through acetylation or deacetylation of the N-terminal tail. CRISPR dCas9 fusions with the enzymes that deposit or remove these modifications, Histone Acetyltransferase (HAT) domains or Histone De-ACetylase (HDAC) domains have been reported in the literature, and these offer an alternative epigenetic programming method we will use if the methylase/demethylase fails. We will also test the Type III CpG island for TET-mediated demethylation: it is methylated and not DAC-responsive, but it may still be an important regulatory element for NRG1 (FIG. 8) and may respond to enforced TET-mediated demethylation. By linking computational predictions with functional tests in our in vitro primary human cell culture we will be able to conclusively validate the differentially methylated regions identified.

Example 3

Neuregulin-1 is an EGF-domain containing signaling protein ligand that binds to ErbB1-4 receptor tyrosine kinases to carry out its function. There are four members of this receptor family, but ErbB3 (or Heregulin-3, HER3) and ErbB4 (or Heregulin-4, or HER4) have been implicated in NRG1 signaling in the nervous system. When activated, ErbB receptors become phosphorylated and transduce their signal through pathways like RAS-ERK cascades and Akt signaling pathways. Our NRG1-responsive in vitro model is ideally suited to determine the NRG1 receptor.

We will harvest stem cells after exposure to 200 ng/ml NRG1 peptide (an activating dose, FIGS. 7A,B,C) and run Western blot to be probed with anti-phosphor-ErbB1 (EGFR), ErbB2, ErbB3, and ErbB4. We expect either ErbB3 or ErbB4 to give the strongest phospho-signal upon NRG1 treatment (compared to vehicle-only controls) but we will examine all four family members. This approach has been successfully used to define the NRG1 receptor in mouse, rat and MCF-7 cancer cells.

Figure 10:
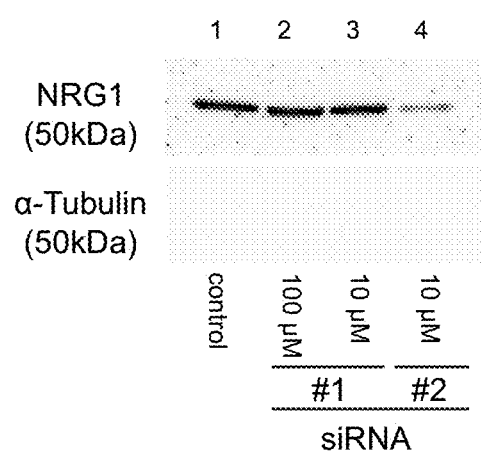
FIG. 10 shows a Western blot showing RNAi knockdown of NRG1 in primary human stem cells. SiRNA #2 is much more effective (lane 4) than siRNA #1 (lanes 2 and 3). Control, untreated cells.

Knockdown of putative NRG1 receptor (functional test). We have successfully knocked down NRG1 itself by siRNA in primary human cells (FIG. 10) so the next step is to inactivate the candidate receptor(s). Pre-validated siRNAs for all human genes are commercially available; we used two such siRNAs in FIG. 10. For example, there are commercially available siRNAs for ErbB3 and ErbB4; many of these are 'silencer select' which is their highest level of validation. The experiment will be to inactivate the receptor, then stimulate with NRG1 β-peptide (as in FIGS. 7A,B,C) and look for abrogation of the differentiation increase. As a positive control we will inactivate NRG1 itself as already performed (FIG. 10) but we expect that the differentiation defect from NRG1 knockdown will be reversed upon stimulation with NRG1 β-peptide. Alternative Strategies. If no ErbB proteins are shown to provide NRG1-inducible phosphorylation, we will test other concentrations of NRG1 peptide corresponding to the physiological range (FIGS. 7A,B,C). If we observe no ErbB receptor activation responding to NRG1 treatment, then a non-cannonical pathway must be involved. ErbB2 has been known to partner with other co-receptors to make functional signaling complexes, and may transduce the signal by phosphorylating those partners (not themselves). Therefore we will identify binding partners of ErbB molecules in primary human stem cell culture by crosslinking, immunoprecipitation, and mass spectrometry. Alternative knockdown. If knockdown fails by siRNA, we will use the classical nuclease version of CRISPR-Cas9 to perform candidate receptor knockout in our cell lines, to see which abrogate response to NRG1 β-peptide. Conclusions. Since the pathways invoked by NRG1 in adipose tissue are unknown at this time, we will perform initial characterizations of which receptors are activated, an important first step towards comprehensive characterization of the pathways involved.

Example 4

The importance of sex differences and gender balance in research has recently been an area of emphasis. Most importantly, sex differences in adipose function between depots, including sex differences in adipocyte size and differentiation from precursor cells, are being discovered. Because our proposal involves primary human adult adipose-derived stem cells from specific depots (Table 2), it is an ideal model system in which to investigate these differences. We therefore will test both sexes for our work and track the donor sex along with other important variables like the depot, donor age, and whether or not they are diabetic (Table 2). We will test male and female mice, to provide a first view of the sex-dependent effect of NRG1 on adipose depots in vivo.

Each of the following references is incorporated herein by reference in its entirety.

Ogden, C. L., Carroll, M. D., Kit, B. K. & Flegal, K. M. Prevalence of childhood and adult obesity in the United States, 2011-2012. *Jama* 311, 806-814, (2014).

Snel, M. et al. Ectopic Fat and Insulin Resistance: Pathophysiology and Effect of Diet and Lifestyle Interventions. *Int J Endocrinol*, (2012).

Astrup, A. & Finer, N. Redefining type 2 diabetes: 'diabesity' or 'obesity dependent diabetes mellitus'? *Obesity reviews: an official journal of the International Association for the Study of Obesity* 1, 57-59 (2000).

Poirier, P. & Eckel, R. H. Obesity and cardiovascular disease. *Current atherosclerosis reports* 4, 448-453 (2002).

Roberts, D. L., Dive, C. & Renehan, A. G. Biological mechanisms linking obesity and cancer risk: new perspectives. *Annual review of medicine* 61, 301-316, (2010).

Drenick, E. J., Bale, G. S., Seltzer, F. & Johnson, D. G. Excessive mortality and causes of death in morbidly obese men. *Jama* 243, 443-445 (1980).

Engeland, A., Bjorge, T., Sogaard, A. J. & Tverdal, A. Body mass index in adolescence in relation to total mortality: 32-year follow-up of 227,000 Norwegian boys and girls. *American journal of epidemiology* 157, 517-523 (2003).

Virtue, S. & Vidal-Puig, A. Adipose tissue expandability, lipotoxicity and the Metabolic Syndrome—an allostatic perspective. *Biochimica et biophysica acta* 1801, 338-349, (2010).

Gustafson, B. & Smith, U. Regulation of white adipogenesis and its relation to ectopic fat accumulation and cardiovascular risk. Atherosclerosis 241, 27-35, (2015).

Kloting, N. et al. Insulin-sensitive obesity. *Am J Physiol Endocrinol Metab* 299, E506-515, (2010).

Arner, E. et al. Adipocyte turnover: relevance to human adipose tissue morphology. *Diabetes* 59, 105-109, (2010).

Gustafson, B., Hedjazifar, S., Gogg, S., Hammarstedt, A. & Smith, U. Insulin resistance and impaired adipogenesis. *Trends Endocrin Met* 26, 193-200, (2015).

Reaven, G. M. Role of insulin resistance in human disease (syndrome X): an expanded definition. *Annual review of medicine* 44, 121-131, (1993).

Bluher, M. The distinction of metabolically 'healthy' from 'unhealthy' obese individuals. *Curr Opin Lipidol* 21, 38-43, (2010).

Ortega, F. B. et al. The intriguing metabolically healthy but obese phenotype: cardiovascular prognosis and role of fitness. *Eur Heart J* 34, 389-397, (2013).

Goncalves, C. G., Glade, M. J. & Meguid, M. M. Metabolically healthy obese individuals: Key protective factors. *Nutrition* 32, 14-20, (2016).

Despres, J. P. & Lemieux, I. Abdominal obesity and metabolic syndrome. *Nature* 444, 881-887, (2006).

Drel, V. R. et al. The leptin-deficient (ob/ob) mouse: a new animal model of peripheral neuropathy of type 2 diabetes and obesity. *Diabetes* 55, 3335-3343, (2006).

Ingalls, A. M., Dickie, M. M. & Snell, G. D. Obese, a new mutation in the house mouse. *J Hered* 41, 317-318 (1950).

Kim, J. Y. et al. Obesity-associated improvements in metabolic profile through expansion of adipose tissue. *Journal of Clinical Investigation* 117, 2621-2637, (2007).

Lessard, J. et al. Low abdominal subcutaneous preadipocyte adipogenesis is associated with visceral obesity, visceral adipocyte hypertrophy, and a dysmetabolic state. *Adipocyte* 3, 197-205, (2014).

Virtue, S. & Vidal-Puig, A. It's not how fat you are, it's what you do with it that counts. *PLoS Biol* 6, e237, (2008).

Tchoukalova, Y. D. et al. Subcutaneous adipocyte size and body fat distribution. *The American journal of clinical nutrition* 87, 56-63 (2008).

Aust, L. et al. Yield of human adipose-derived adult stem cells from liposuction aspirates. *Cytotherapy* 6, 7-14 (2004).

Muir, L. A. et al. Adipose tissue fibrosis, hypertrophy, and hyperplasia: Correlations with diabetes in human obesity. *Obesity* (Silver Spring) 24, 597-605, (2016).

Tchoukalova, Y., Koutsari, C. & Jensen, M. Committed subcutaneous preadipocytes are reduced in human obesity. *Diabetologia* 50, 151-157, (2007).

Isakson, P., Hammarstedt, A., Gustafson, B. & Smith, U. Impaired preadipocyte differentiation in human abdominal obesity: role of Wnt, tumor necrosis factor-alpha, and inflammation. *Diabetes* 58, 1550-1557, (2009).

Gustafson, B. & Smith, U. The WNT inhibitor Dickkopf 1 and bone morphogenetic protein 4 rescue adipogenesis in hypertrophic obesity in humans. *Diabetes* 61, 1217-1224, (2012).

Arner, P., Arner, E., Hammarstedt, A. & Smith, U. Genetic Predisposition for Type 2 Diabetes, but Not for Overweight/Obesity, Is Associated with a Restricted Adipogenesis. *PLoS one* 6, e18284, (2011).

Pellegrinelli, V., Carobbio, S. & Vidal-Puig, A. Adipose tissue plasticity: how fat depots respond differently to pathophysiological cues. *Diabetologia* 59, 1075-1088, (2016).

Ennequin, G. et al. Neuregulin 1 affects leptin levels, food intake and weight gain in normal-weight, but not obese, db/db mice. *Diabetes Metab* 41, 168-172, (2015).

Ennequin, G. et al. Neuregulin 1 Improves Glucose Tolerance in db/db Mice. *PLoS one* 10, e0130568, (2015).

Snodgrass-Belt, P., Gilbert, J. L. & Davis, F. C. Central administration of transforming growth factor-alpha and neuregulin-1 suppress active behaviors and cause weight loss in hamsters. *Brain Res* 1038, 171-182, (2005).

Gao, R. et al. A Phase II, randomized, double-blind, multicenter, based on standard therapy, placebo-controlled study of the efficacy and safety of recombinant human neuregulin-1 in patients with chronic heart failure. *J Am Coll Cardiol* 55, 1907-1914, (2010).

Jabbour, A. et al. Parenteral administration of recombinant human neuregulin-1 to patients with stable chronic heart failure produces favourable acute and chronic haemodynamic responses. *Eur J Heart Fail* 13, 83-92, (2011).

Caillaud, K. et al. Neuregulin 1 improves glucose tolerance in adult and old rats. *Diabetes Metab* 42, 96-104, (2016).

Ennequin, G. et al. Neuregulin 1 improves complex 2-mediated mitochondrial respiration in skeletal muscle of healthy and diabetic mice. *Sci Rep* 7, 1742, (2017).

Paffhausen, E. S. et al. Discovery of a stem-like multipotent cell fate. *American Journal of Stem Cells* 7, 25-37 (2018).

Zuk, P. A. et al. Human adipose tissue is a source of multipotent stem cells. *Molecular biology of the cell* 13, 4279-4295, (2002).

Zuk, P. A. et al. Multilineage cells from human adipose tissue: implications for cell-based therapies. *Tissue engineering* 7, 211-228, (2001).

Tang, Q. Q. & Lane, M. D. Adipogenesis: From Stem Cell to Adipocyte. *Annu Rev Biochem* 81, 715-736, (2012).

Takada, H. et al. Methylome, transcriptome, and PPAR-gamma cistrome analyses reveal two epigenetic transitions in fat cells. *Epigenetics: official journal of the DNA Methylation Society* 9, 1195-1206, (2014).

Boquest, A. C., Noer, A. & Collas, P. Epigenetic programming of mesenchymal stem cells from human adipose tissue. *Stem Cell Rev* 2, 319-329, (2006).

Noer, A., Sorensen, A. L., Boquest, A. C. & Collas, P. Stable CpG hypomethylation of adipogenic promoters in freshly isolated, cultured, and differentiated mesenchymal stem cells from adipose tissue. *Molecular biology of the cell* 17, 3543-3556, (2006).

Sorensen, A. L., Jacobsen, B. M., Reiner, A. H., Andersen, I. S. & Collas, P. Promoter DNA Methylation Patterns of Differentiated Cells Are Largely Programmed at the Progenitor Stage. *Molecular biology of the cell* 21, 2066-2077, (2010).

van den Dungen, M. W., Murk, A. J., Kok, D. E. & Steegenga, W. T. Comprehensive DNA Methylation and Gene Expression Profiling in Differentiating Human Adipocytes. *Journal of Cellular Biochemistry* (2016).

Mikkelsen, T. S. et al. Comparative epigenomic analysis of murine and human adipogenesis. *Cell* 143, 156-169, (2010).

Chen, Y., Pan, R. & Pfeifer, A. Fat tissues, the brite and the dark sides. *Pflugers Arch* 468, 1803-1807, (2016).

Chondronikola, M. & Sidossis, L. S. Brown and beige fat: From molecules to physiology. *Biochimica et biophysica acta*, (2018).

Carobbio, S., Guenantin, A. C., Samuelson, I., Bahri, M. & Vidal-Puig, A. Brown and beige fat: From molecules to physiology and pathophysiology. *Biochimica et biophysica acta*, (2018).

Jun, H. et al. An immune-beige adipocyte communication via nicotinic acetylcholine receptor signaling. *Nat Med* 24, 814-822, (2018).

Christian, M. Transcriptional fingerprinting of "browning" white fat identifies NRG4 as a novel adipokine. *Adipocyte* 4, 50-54, (2015).

Ma, Y., Gao, M. & Liu, D. Preventing High Fat Diet-induced Obesity and Improving Insulin Sensitivity through Neuregulin 4 Gene Transfer. *Sci Rep* 6, 26242, (2016).

Smith, J. K. Exercise, Obesity and CNS Control of Metabolic Homeostasis: A Review. *Front Physiol* 9, 574, (2018).

Ahima, R. S. Adipose tissue as an endocrine organ. *Obesity* 14, 242-249 (2006).

Tchkonia, T. et al. Mechanisms and Metabolic Implications of Regional Differences among Fat Depots. *Cell Metabolism* 17, 644-656, (2013).

Van Harmelen, V. et al. Leptin secretion from subcutaneous and visceral adipose tissue in women. *Diabetes* 47, 913-917 (1998).

Atzmon, G. et al. Differential gene expression between visceral and subcutaneous fat depots. *Horm Metab Res* 34, 622-628, (2002).

Friend, D. M. et al. Basal Ganglia Dysfunction Contributes to Physical Inactivity in Obesity. *Cell Metab* 25, 312-321, (2017).

Licholai, J. A. et al. Why Do Mice Overeat High-Fat Diets? How High-Fat Diet Alters the Regulation of Daily Caloric Intake in Mice. *Obesity* 26, 1026-1033, (2018).

Matikainen-Ankney, B. A. & Kravitz, A. V. Persistent effects of obesity: a neuroplasticity hypothesis. *Ann N Y Acad Sci*, (2018).

Nguyen, K. P. et al. Feeding Experimentation Device (FED): Construction and Validation of an Open-source Device for Measuring Food Intake in Rodents. *Journal of visualized experiments:JoVE*, (2017).

Reznikoff, C. A., Bertram, J. S., Brankow, D. W. & Heidelberger, C. Quantitative and qualitative studies of chemical transformation of cloned C3H mouse embryo cells sensitive to postconfluence inhibition of cell division. *Cancer Res* 33, 3239-3249 (1973).

Green, H. & Meuth, M. An established pre-adipose cell line and its differentiation in culture. *Cell* 3, 127-133 (1974).

Todaro, G. J. & Green, H. Quantitative studies of the growth of mouse embryo cells in culture and their development into established lines. *The Journal of cell biology* 17, 299-313 (1963).

Cotsarelis, G., Sun, T. T. & Lavker, R. M. Label-Retaining Cells Reside in the Bulge Area of Pilosebaceous Unit—Implications for Follicular Stem-Cells, Hair Cycle, and Skin Carcinogenesis. *Cell* 61, 1329-1337, (1990).

Blanpain, C., Lowry, W. E., Geoghegan, A., Polak, L. & Fuchs, E. Self-renewal, multipotency, and the existence of two cell populations within an epithelial stem cell niche. *Cell* 118, 635-648, (2004).

Potten, C. S., Booth, C. & Pritchard, D. M. The intestinal epithelial stem cell: the mucosal governor. *Int J Exp Pathol* 78, 219-243, (1997).

Arai, F. et al. Tie2/angiopoietin-1 signaling regulates hematopoietic stem cell quiescence in the bone marrow niche. *Cell* 118, 149-161, (2004).

Mira, H. et al. Signaling through BMPR-IA Regulates Quiescence and Long-Term Activity of Neural Stem Cells in the Adult Hippocampus. *Cell Stem Cell* 7, 78-89, (2010).

Li, L. & Clevers, H. Coexistence of quiescent and active adult stem cells in mammals. *Science* 327, 542-545, (2010).

Jones, P. A. & Taylor, S. M. Cellular differentiation, cytidine analogs and DNA methylation. *Cell* 20, 85-93 (1980).

Frohling, S. et al. Identification of driver and passenger mutations of FLT3 by high-throughput DNA sequence analysis and functional assessment of candidate alleles. *Cancer Cell* 12, 501-513, (2007).

Kalari, S. & Pfeifer, G. P. Identification of Driver and Passenger DNA Methylation in Cancer by Epigenomic Analysis. *Adv Genet* 70, 277-308, (2010).

Zhang, L., Komurov, K., Wright, W. E. & Shay, J. W. Identification of novel driver tumor suppressors through functional interrogation of putative passenger mutations in colorectal cancer. *Int J Cancer* 132, 732-737, (2013).

Kwan, R., Looi, K. & Omary, M. B. Absence of keratins 8 and 18 in rodent epithelial cell lines associates with keratin gene mutation and DNA methylation: Cell line selective effects on cell invasion. *Exp Cell Res* 335, 12-22, (2015).

Ferrario, C. et al. Metallothionein 1G acts as an oncosupressor in papillary thyroid carcinoma. *Lab Invest* 88, 474-481, (2008).

Falls, D. L. Neuregulins: functions, forms, and signaling strategies. *Exp Cell Res* 284, 14-30, (2003).

Mei, L. & Xiong, W. C. Neuregulin 1 in neural development, synaptic plasticity and schizophrenia. *Nat Rev Neurosci* 9, 437-452, (2008).

Geisberg, C. A. et al. Circulating neuregulin-1beta levels vary according to the angiographic severity of coronary artery disease and ischemia. *Coron Artery Dis* 22, 577-582, (2011).

Moondra, V. et al. Serum Neuregulin-lbeta as a Biomarker of Cardiovascular Fitness. *Open Biomark J* 2, 1-5, (2009).

Kern, M. et al. C57BL/6JRj mice are protected against diet induced obesity (DIO). *Biochemical and biophysical research communications* 417, 717-720, (2012).

Chusyd, D. E., Wang, D. H., Huffman, D. M. & Nagy, T. R. Relationships between Rodent white Adipose Fat Pads and Human white Adipose Fat Depots. *Front Nutr* 3, (2016).

Parlee, S. D., Lentz, S. I., Mori, H. & MacDougald, O. A. Quantifying size and number of adipocytes in adipose tissue. *Methods Enzymol* 537, 93-122, (2014).

Pascual-Serrano, A. et al. Grape seed proanthocyanidin supplementation reduces adipocyte size and increases adipocyte number in obese rats. *Int J Obesity* 41, 1246-1255, (2017).

Yamamoto, N. et al. Isolation of multipotent stem cells from mouse adipose tissue. *J Dermatol Sci* 48, 43-52, (2007).

Taha, M. F. & Hedayati, V. Isolation, identification and multipotential differentiation of mouse adipose tissue derived stem cells. *Tissue Cell* 42, 211-216, (2010).

Winzell, M. S. & Ahren, B. The high-fat diet-fed mouse: a model for studying mechanisms and treatment of impaired glucose tolerance and type 2 diabetes. *Diabetes* 53 Suppl 3, S215-219 (2004).

Tschop, M. H. et al. A guide to analysis of mouse energy metabolism. *Nat Methods* 9, 57-63, (2011).

Frontini, A. & Cinti, S. Distribution and Development of Brown Adipocytes in the Murine and Human Adipose Organ. *Cell Metabolism* 11, 253-256, (2010).

Dekker, J. & Mirny, L. The 3D Genome as Moderator of Chromosomal Communication. *Cell* 164, 1110-1121, (2016).

Denker, A. & de Laat, W. The second decade of 3C technologies: detailed insights into nuclear organization. *Genes & development* 30, 1357-1382, (2016).

Zhang, L. et al. DNA Methylation Landscape Reflects the Spatial Organization of Chromatin in Different Cells. *Biophys J* 113, 1395-1404, (2017).

Gondor, A., Rougier, C. & Ohlsson, R. High-resolution circular chromosome conformation capture assay. *Nat Protoc* 3, 303-313, (2008).

Zhao, Z. et al. Circular chromosome conformation capture (4C) uncovers extensive networks of epigenetically regulated intra- and interchromosomal interactions. *Nature genetics* 38, 1341-1347, (2006).

Wurtele, H. & Chartrand, P. Genome-wide scanning of HoxB1-associated loci in mouse ES cells using an open-ended Chromosome Conformation Capture methodology. *Chromosome Res* 14, 477-495, (2006).

Lomvardas, S. et al. Interchromosomal interactions and olfactory receptor choice. *Cell* 126, 403-413, (2006).

Jian, X. & Felsenfeld, G. Insulin promoter in human pancreatic beta cells contacts diabetes susceptibility loci and regulates genes affecting insulin metabolism. *Proceedings of the National Academy of Sciences of the United States of America* 115, E4633-E4641, (2018).

Splinter, E., de Wit, E., van de Werken, H. J. G., Klous, P. & de Laat, W. Determining long-range chromatin interactions for selected genomic sites using 4C-seq technology: From fixation to computation. *Methods* 58, 221-230, (2012).

van de Werken, H. J. et al. Robust 4C-seq data analysis to screen for regulatory DNA interactions. *Nat Methods* 9, 969-972, (2012).

Raviram, R. et al. 4C-ker: A Method to Reproducibly Identify Genome-Wide Interactions Captured by 4C-Seq Experiments. *PLoS Comput Biol* 12, e1004780, (2016).

Kolovos, P. et al. Targeted Chromatin Capture (T2C): a novel high resolution high throughput method to detect genomic interactions and regulatory elements. *Epigenet Chromatin* 7, (2014).

Dixon, J. R. et al. Topological domains in mammalian genomes identified by analysis of chromatin interactions. *Nature* 485, 376-380, (2012).

Cong, L. et al. Multiplex Genome Engineering Using CRISPR/Cas Systems. *Science* 339, 819-823, (2013).

Mali, P. et al. RNA-guided human genome engineering via Cas9. *Science* 339, 823-826, (2013).

Jinek, M. et al. RNA-programmed genome editing in human cells. *Elife* 2, (2013). Ledford, H. CRISPR: gene editing is just the beginning. *Nature* 531, 156-159, (2016).

Tahiliani, M. et al. Conversion of 5-methylcytosine to 5-hydroxymethylcytosine in mammalian DNA by MLL partner TET1. *Science* 324, 930-935, (2009).

Xu, X. et al. A CRISPR-based approach for targeted DNA demethylation. *Cell Discov* 2, 16009, (2016).

Liu, X. S. et al. Editing DNA Methylation in the Mammalian Genome. *Cell* 167, 233-247 e217, (2016).

Law, J. A. & Jacobsen, S. E. Establishing, maintaining and modifying DNA methylation patterns in plants and animals. *Nature reviews. Genetics* 11, 204-220, (2010).

Vojta, A. et al. Repurposing the CRISPR-Cas9 system for targeted DNA methylation. *Nucleic acids research*, gkw159 (2016).

McDonald, J. I. et al. Reprogrammable CRISPR/Cas9-based system for inducing site-specific DNA methylation. *Biol Open* 5, 866-874, (2016).

Rothbart, S. B. & Strahl, B. D. Interpreting the language of histone and DNA modifications. *Biochimica et biophysica acta* 1839, 627-643, (2014).

Hilton, I. B. et al. Epigenome editing by a CRISPR-Cas9-based acetyltransferase activates genes from promoters and enhancers. *Nature biotechnology* 33, 510-517 (2015).

Kwon, D. Y., Zhao, Y. T., Lamonica, J. M. & Zhou, Z. Locus-specific histone deacetylation using a synthetic CRISPR-Cas9-based HDAC. *Nat Commun* 8, (2017).

Wang, Y. H. et al. Microporation Is a Valuable Transfection Method for Gene Expression in Human Adipose Tissue-derived Stem Cells. *Mol Ther* 17, 302-308, (2009).

Biederman, M. K. et al. Discovery of the First Germline-Restricted Gene by Subtractive Transcriptomic Analysis in the Zebra Finch, Taeniopygia guttata. *Current Biology* 28, 1620-1627.e1625, (2018).

Rupert, C. E. & Coulombe, K. L. The roles of neuregulin-1 in cardiac development, homeostasis, and disease. *Biomark Insights* 10, 1-9, (2015).

Iwakura, Y. & Nawa, H. ErbB1-4-dependent EGF/neuregulin signals and their cross talk in the central nervous system: pathological implications in schizophrenia and Parkinson's disease. *Front Cell Neurosci* 7, 4, (2013).

Kovacs, T., Bansagi, B., Kelemen, O. & Ken, S. Neuregulin 1-Induced AKT and ERK Phosphorylation in Patients with Fragile X Syndrome (FXS) and Intellectual Disability Associated with Obstetric Complications. *J Mol Neurosci* 54, 119-124, (2014).

Herrero, A., Casar, B., Colon-Bolea, P., Agudo-Ibanez, L. & Crespo, P. Defined spatiotemporal features of RASERK signals dictate cell fate in MCF-7 mammary epithelial cells. *Molecular biology of the cell* 27, 1958-1968, (2016).

Nagashima, T. et al. Quantitative transcriptional control of ErbB receptor signaling undergoes graded to biphasic response for cell differentiation. *The Journal of biological chemistry* 282, 4045-4056, (2007).

Aghajanian, H. et al. Coronary vasculature patterning requires a novel endothelial ErbB2 holoreceptor. *Nat Commun* 7, 12038, (2016).

Clayton, J. A. & Collins, F. S. Policy: NIH to balance sex in cell and animal studies. *Nature* 509, 282-283 (2014).

Karastergiou, K. & Fried, S. K. Cellular Mechanisms Driving Sex Differences in Adipose Tissue Biology and Body Shape in Humans and Mouse Models. *Adv Exp Med Biol* 1043, 29-51, (2017).

National Institutes of Health Guidelines on Human Subjects Research. https://humansubjects.nih.gov/walkthrough-investigatorkabpanel11. (2018).

Schmid, R. S. et al. Neuregulin 1-erbB2 signaling is required for the establishment of radial glia and their transformation into astrocytes in cerebral cortex. *Proceedings of the National Academy of Sciences of the United States of America* 100, 4251-4256, (2003).

Sato, T. et al. Neuregulin 1 Type II-ErbB Signaling Promotes Cell Divisions Generating Neurons from Neural Progenitor Cells in the Developing Zebrafish Brain. *PloS one* 10, (2015).

Pirotte, D., Wislet-Gendebien, S., Cloes, J. M. & Rogister, B. Neuregulin-1 modulates the differentiation of neural stem cells in vitro trough an interaction with the Swi/Snf complex. *Mol Cell Neurosci* 43, 72-80, (2010).

Bersell, K., Arab, S., Haring, B. & Kuhn, B. Neuregulinl/ErbB4 Signaling Induces Cardiomyocyte Proliferation and Repair of Heart Injury. *Cell* 138, 257-270, (2009).

Wang, Z. et al. Neuregulin-1 enhances differentiation of cardiomyocytes from embryonic stem cells. *Med Biol Eng Comput* 47, 41-48, doi:10.1007/s11517-008-0383-2 (2009).

Sequence Listing

Applicants incorporate by reference the material contained in the accompanying computer readable Sequence Listing identified as 023783.62_ST25.txt, having a file creation date of Oct. 22, 2019 11:25 A.M. and file size of 940 bytes.

```
human NRG1 peptide fragment-
                                    SEQ ID NO: 1
SHLVKCAEKEKTFCVNGGECFMVKDLSNPSRYLCKCPNEFTGDRCQ

NYVMASFYKHLGIEFMEAE
```

The sequences of all of the isoforms of full-length human Neuregulin-1 protein types I, II, III, IV, V and VI are incorporated herein—see NRG1 neuregulin 1 [Homo sapiens (human)], Gene ID: 3084 in NCBI database (https://www.ncbi.nlm.nih.gov/gene/3084).

What is claimed is:

1. A method for increasing the differentiation of preadipocytes into adipocytes, the method comprising exposing the preadipocytes to Neuregulin-1 under conditions sufficient to promote differentiation of the preadipocytes into adipocytes; wherein the Neuregulin-1 is NRG1 β.

2. The method of claim 1, wherein the Neuregulin-1 is the Type III isoform of NRG1β.

3. The method of claim 1, wherein the Neuregulin-1 is a fragment of NRG1 β comprising an EGF-binding domain.

4. The method of claim 3, wherein the fragment of NRG1 β is SEQ ID NO: 1.

5. The method of claim 1, wherein the NRG1 β is provided at a concentration of about 1 ng/ml to about 500 ng/ml.

6. The method of claim 1, wherein the preadipocytes are white adipose tissue (WAT) preadipocytes.

7. The method of claim 1, wherein the method is performed in vitro or in vivo.

8. The method of claim 7, wherein when the method is performed in vivo, the increase in the differentiation of the preadipocytes into adipocytes results in an increase in the number of adipocytes.

9. The method of claim 7, wherein when the method is performed in vivo, exposing the preadipocytes to NRG1 β results in at least one of the following: increased leptin levels, lowered inflammation, decreased blood sugar, increased insulin sensitivity, lowered insulin levels, decreased hypertension, resolution of hyperlipidemia, lowered bodyweight.

10. A method for increasing the differentiation of adipose-derived stem cells (ASCs) into adipocytes, the method comprising exposing the ASCs to Neuregulin-1 under conditions sufficient to promote differentiation of the ASCs into adipocytes; wherein the Neuregulin-1 is NRG1 β.

11. The method of claim 10, wherein the Neuregulin-1 is the Type III isoform of NRG1 β.

12. The method of claim 10, wherein the Neuregulin-1 is a fragment of NRG1 β comprising an EGF-binding domain.

13. The method of claim 12, wherein the fragment of NRG1 β is SEQ ID NO: 1.

14. The method of claim 10, wherein the NRG1 β is provided at a concentration of about 1 ng/ml to about 500 ng/ml.

15. The method of claim 10, wherein the ASCs are white adipose tissue (WAT) ASCs.

16. The method of claim 10, wherein the method is performed in vitro or in vivo.

17. The method of claim 16, wherein when the method is performed in vivo, the increase in the differentiation of the ASCs into adipocytes results in an increase in the number of adipocytes.

18. The method of claim 16, wherein when the method is performed in vivo, exposing the ASCs to NRG1 β results in at least one of the following: increased leptin levels, lowered inflammation, decreased blood sugar, increased insulin sensitivity, lowered insulin levels, decreased hypertension, resolution of hyperlipidemia, lowered bodyweight.

* * * * *

SEQUENCE LISTING

```
<160> NUMBER OF SEQ ID NOS: 1

<210> SEQ ID NO 1
<211> LENGTH: 65
<212> TYPE: PRT
<213> ORGANISM: Homo sapiens

<400> SEQUENCE: 1

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys His Leu Gly Ile Glu Phe Met Glu Ala
    50                  55                  60

Glu
65
```